US011236154B2

(12) United States Patent
Yu et al.

(10) Patent No.: US 11,236,154 B2
(45) Date of Patent: Feb. 1, 2022

(54) CARBOHYDRATE ANTIBODIES, PHARMACEUTICAL COMPOSITIONS AND USES THEREOF

(71) Applicant: OBI PHARMA, INC., Taipei (TW)

(72) Inventors: Cheng-Der Tony Yu, Taipei (TW); Jiann-Shiun Lai, Taipei (TW); I-Ju Chen, Taipei (TW)

(73) Assignee: OBI PHARMA INC., Taipei (TW)

( * ) Notice: Subject to any disclaimer, the term of this patent is extended or adjusted under 35 U.S.C. 154(b) by 334 days.

(21) Appl. No.: 16/547,009

(22) Filed: Aug. 21, 2019

(65) Prior Publication Data

US 2020/0048334 A1 Feb. 13, 2020

Related U.S. Application Data

(62) Division of application No. 15/288,562, filed on Oct. 7, 2016, now Pat. No. 10,501,532.

(60) Provisional application No. 62/238,680, filed on Oct. 7, 2015.

(51) Int. Cl.
| | | |
|---|---|---|
| A61K 39/395 | (2006.01) | |
| C07K 16/18 | (2006.01) | |
| A61P 35/00 | (2006.01) | |
| C07K 16/44 | (2006.01) | |
| C07K 16/30 | (2006.01) | |
| A61K 39/00 | (2006.01) | |

(52) U.S. Cl.
CPC ............ C07K 16/18 (2013.01); A61P 35/00 (2018.01); C07K 16/30 (2013.01); C07K 16/44 (2013.01); *A61K 2039/505* (2013.01); *A61K 2039/80* (2018.08); *C07K 2317/24* (2013.01); *C07K 2317/565* (2013.01); *C07K 2317/567* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 4,816,567 | A | 3/1989 | Cabilly et al. |
|---|---|---|---|
| 5,225,539 | A | 7/1993 | Winter |
| 5,585,089 | A | 12/1996 | Queen et al. |
| 5,693,761 | A | 12/1997 | Queen et al. |
| 5,693,762 | A | 12/1997 | Queen et al. |
| 6,548,640 | B1 | 4/2003 | Winter |
| 6,982,321 | B2 | 1/2006 | Winter |
| 2004/0087651 | A1 | 5/2004 | Pereira Da Fonseca et al. |
| 2010/0098692 | A1 | 4/2010 | Theuer et al. |
| 2011/0256154 | A1 | 10/2011 | Vincent et al. |
| 2014/0212427 | A1 | 7/2014 | Song |

FOREIGN PATENT DOCUMENTS

| CN | 104 693 305 | 6/2015 |
|---|---|---|
| EP | 125023 | 11/1984 |
| EP | 184187 | 12/1985 |
| EP | 171496 | 2/1986 |
| EP | 173494 | 3/1986 |
| EP | 0519596 | 12/1992 |
| TW | 201546092 | 12/2015 |
| WO | 8601533 | 3/1986 |
| WO | 8702671 | 5/1987 |
| WO | 2005010049 | 2/2005 |
| WO | 2006084050 | 8/2006 |
| WO | 201515629 | 2/2015 |
| WO | 2015143123 | 9/2015 |
| WO | 2015143126 | 9/2015 |

OTHER PUBLICATIONS

U.S. Appl. No. 15/288,562, files Oct. 7, 2016, Pending.
Supplementary European Search Report issued in EP Application No. EP 16 85 4440, dated Apr. 1, 2019.
International Search Report and Written Opinion of International Patent Application No. PCT/US2016/056032, dated Jan. 24, 2017.
Sally Ward, et al., "Binding Activities of a Repertoire of Single Immunoglobulin Variable Domains Secreted from *Excherichia coli*", Nature, 1989, vol. 341, pp. 544-546.
Robert E. Bird, et al., "Single-Chain Antigen-Binding Proteins", Science, 1988, vol. 85, pp. 5879-5883.
Alison Tutt, et al., "Trispecific F (ab') 3 Derivatives that Use Cooperative Signaling Via the TCR/CD3 Complex and co::; to Activate and Redirect Resting Cytotoxic T Cells", The Journal of Immunology, 1991, vol. 147, pp. 60-69.
Peter Kuter, et al., "A Revival of Bispecific Antibodies", Trends in Biotechnology, May 2004, vol. 22, pp. 238-244.
E. A. Kabat, et al., "Sequences of Proteins of Immunological Interest", National Institute of Health Publication, U.S. Department of Health and Human Services, 1991, NIH Publication No. 91-3242.
Cyrus Biology, Chothia, Science, et al., vol. 196, "Canonical pp. 901-917. Structures for the Hypervariable Regions of Immunoglobulins", Journal of Molecular Biology, Science. vol. 196, pp. 901-917.
Sherie Science, L. 1984, Morrison, vol. 81, pp: "Transfectomas 6851-6855. Provide Novel Chimeric Antibodies", vol. Proceeding National Academic of Science, 1984, vol. 81, pp. 6851-6855.
Vernon T. OI, et al., "Chimeric Antibodies", Bio Techniques, 1986, vol. 4, pp. 214-220.

(Continued)

*Primary Examiner* — Meera Natarajan
(74) *Attorney, Agent, or Firm* — Michael X. Ye; Rimon Law

(57) ABSTRACT

The present invention provides antibodies or the antigen-binding portion thereof to a tumor-associate carbohydrate antigen. Also disclosed herein are pharmaceutical compositions and methods for the inhibition of cancer cells in a subject in need thereof. The pharmaceutical compositions comprise an antibody or an antigen-binding portion thereof and at least one pharmaceutically acceptable carrier.

17 Claims, 37 Drawing Sheets

Specification includes a Sequence Listing.

(56) References Cited

OTHER PUBLICATIONS

Peter T. Jones, et al., "Replacing the Complementarity Determining Regions in a Human Antipodes With Those From a Mouse", Nature, 1986, vol. 321, pp. 552-525.
Martine Verhoeyen, et al., "Reshaping Human Antibodies: Grafting an Antilysozyme Activity", Science, vol. 239, pp. 1534.
Catherine B. Beidler, et al., "Cloning and High Level Expression of a Chimeric Antibody with Specificity for Human Carcinoembryonic Antigen", The Journal of Immunology, 1988, vol. 141, pp. 4053-4060.
Sherie L. Morrison, et al., "Chimeric Human Antibody Molecules: Mouse Antigen-Binding Domains with Human Constant Region Domains", Proceeding of National Academic of Sciences, Nov. 1984, vol. 81, pp. 6851-6855.
Marc Better, et al. "*Escherichia coli* Secretion of an Active Chimeric Antigoy Fragment", 1988, vol. 240, pp. 1041-1043.
Alvin Y. Liu, et al. "Chimeric Mouse-Human IgG1 Antibody that can Mediate Lysis of Cancer Cell", Procedding of National Academy of Science, May 1987, vol. 84, pp. 3439-3443.
Alvin Y. Liu, et al. "Production of a Mouse Human Chimeric Monoclonal Antibody to CD20 with Potent Fe-Dependent Biologic Activity". The Journal of Immunology, Nov. 1987, vol. 139, pp. 3521-3526.
Lee K. Sun, et al. "Chimeric Antibody with Human Constant Regions and Mouse Variable Regions Directed Against Carcinoma-Associated Antigen 17-1 A", Jan. 1987, vol. 84, pp. 214-218.
Yushi Nishimura, et al. "Recombinant Human-Mouse Chimeric Monoclonal Antibody Specific for Common Acute Lymphocytic Leukemia Antigen", Cancer Research, Feb. 1987, vol. 47, pp. 999-1005.
Clive R. Wood, et al., "The Synthesis and in Vivo Assembly of Functional Antibodies in Yeast", Apr. 1985, vol. 314, pp. 446-449.
Denise R. Shaw, et al: "Mouse/Human Chimeric Antibodies to a Turner-Associated Antigen: Biologic Activity of the Four Human IgG Subclasses", Journal of National Caner Institute, Dec. 1988, vol. 80, pp. 1553-1559.
Pauline C. Ng, et al.: "Predicting the Effects of Amino Acid Substitutions on Protein Function", The Annual Review of Genomics and Human Genetics, 2006, vol. 7, pp. 61-80.
James U. Bowie, "Deciphering the Message in Protein Sequences: Tolerance to Amino Acid Substitutions", Science, 1990, vol. 247, pp. 1306-1310.
Brian C. Cunningham, "High-Resolution Epitope Mapping of HGH-Receptor Interactions by Alanine-Scanning Mutagenesis", Science, 1989, vol. 244, pp. 1081-1085.
Ausubel (ed.), "Current Protocols in Molecular Biology", John Wiley and Sons, Inc. 1994.

T. Maniatis, E.F. Fritsch and J. Sambrook, "Molecular Cloning: A Laboratory Manual", Cold Spring Harbor Laboratory, Cold Spring, Harbor, 1989, vol. 1.
William R. Pearson, "Using the FASTA Program to Search Protein and DNA Sequence Databases", Methods in Molecular Biology, 1994, vol. 243, pp. 307-331.
Gaston H. Gannet, "Exhaustive Matching of the Entire Protein Sequence Database", Science, Jun. 1992, vol. 256, pp. 1443-1445.
Jay A. Berzofsky et al., "Antigen-Antibody Interactions and Monoclonal Antibodies", In Fundamental Immunology, 1984.
Janis Kuby, "Immunology", Raven Press, New York, 1984.
James D. Marks, "By-Passing Immunization: Building High Affinity Human Antibodies by Chain Shuffling", Biotechnology, Jul. 1992, vol. 10, pp. 779-783.
Robert E. Hawkins, "Selection of Phage Antibodies by Binding Affinity Mimicking Affinity Maturation", Journal of Molecular Biology, 1992, vol. 226, pp. 889-896.
Janaina Fernandes, et al., "Perillyl Alcohol Induces Apoptosis in Human Glioblastoma Multiforme Cells", Oncology Report, 2005, vol. 13, pp. 943-947.
Clovis Orlando Da Fonseca, et al, "Preliminary Results from a Phase 1/11 Study of Perillyl Alcohol Intranasal Administration in Adults with Recurrent Malignant Gliomas", Surgical Neurology, 2008, vol. 70, 259-267.
Clovis Orlando Da Fonseca, et al., "Ras pathway Activation in Gliomas: A Strategic Target for Intranasal Administration of Perillyl Alcohol", Surgical Neurology, 2008, vol. 70, 259-267.
Rintaro Hashizume et al., "New Therapeutic Approach for Brain Tumors: Intranasal Delivery of Telomerase Inhibitor GRN163", Neuroncology, 2008, vol. 10, 112-120.
Beverly A. Teicher, et al., "Tumor Model For Efficacy Determination", Mol Cancer Ther, Oct. 2006, vol. 5, pp. 2435-2443.
Grete Sonderstrup, "Development of Humanized Mince as a Model of Inflammatory Arthritis", Springer Seminars in Immunophathology, 2003, vol. 25, pp. 35-45.
Kriten J. Nikula et al., "Animal Models of Chronic Bronchitis and Their Relevance to Studies of Particle-Induced Disease", Inhalation Toxicology, 2000, vol. 12, pp. 123-153.
Tim Mosmann, "Rapid Colorimetric Assay for Cellular Growth and Survival: Application to Proliferation and Cytotoxicity Assays", Journal of Immunological Methods, 1983, vol. 65, pp. 55-63.
James S. Huston, "Protein Engineering of Antibody Binding Sites: Recovery of Activity in an Anti-digoxin Single-Chain FV Analogue Produce *Escherichia coli*", Proceeding of National Academy of Science, Aug. 1988, vol. 85, pp. 5879-5883.
Lamminmaki, et al., (JBC 2001, vol. 276, pp. 36687-36694).
Vajdos, et al., (J. Mol. Biol. (2002) 320, 415-428).
Chen, et al., (J. Mol. Bio. (1990) 293, 865-881).
Wu, et al., (J. Mol. Biol. (1999) 294, 151-162).
Padlan, et al. (PNAS 1989, 86:5938-5942).
Rudikoff, et al., (Proc Natl Acad. Sci., USA, 1982, vol. 79, p. 1979).
MacCallum, et al., (J. Mol. Biol. 1996, 262, pp. 732-745).
Casset, et al. (BBRC 2003, 307, pp. 198-205).

Gln Ile Thr Leu Lys Glu Ser Gly Pro Thr Leu Val Lys Pro Thr
1               5                    10                    15

Gln Thr Leu Thr Leu Thr Cys Thr Phe Ser Gly Phe Ser Leu Tyr
                20                    25                    30

Thr Phe Asp Met Gly Val Gly Trp Ile Arg Gln Pro Ser Gly Lys
                35                    40                    45

Gly Leu Glu Trp Leu Ala His Ile Trp Trp Asp Asp Asp Lys Tyr
                50                    55                    60

Tyr Asn Pro Ala Leu Lys Ser Arg Leu Thr Ile Ser Lys Asp Thr
                65                    70                    75

Ser Lys Asn Gln Val Val Leu Thr Met Thr Asn Met Asp Pro Val
                80                    85                    90

Asp Thr Ala Thr Tyr Tyr Cys Ala Arg Val Arg Gly Leu His Asp
                95                    100                   105

Tyr Tyr Tyr Trp Phe Ala Tyr
            110

FIGURE 1A

Glu Ile Val Leu Thr Gln Ser Pro Ala Thr Leu Ser Leu Ser Pro
1               5                    10                   15

Gly Glu Arg Ala Thr Leu Ser Cys Arg Ala Ser Ser Ser Val Ser
                20                   25                   30

Tyr Met His Trp Tyr Gln Gln Lys Pro Gly Ser Ser Pro Lys Pro
                35                   40                   45

Trp Ile Tyr Ala Thr Ser Asn Leu Ala Ser Gly Val Pro Ser Arg
                50                   55                   60

Phe Ser Gly Ser Gly Ser Gly Thr Asp Phe Thr Phe Thr Ile Ser
                65                   70                   75

Ser Leu Gln Pro Glu Asp Ile Ala Thr Tyr Tyr Cys Gln Gln Trp
                80                   85                   90

Ser Arg Asn Pro Phe Thr
                95

FIGURE 1B

| Light Chain | Heavy Chain | Optical Density (OD$_{450}$nm) (Binding Affinity) |
|---|---|---|
| Light Chain Variable Region of Chimeric Antibody (SEQ ID No. 58) | Heavy Chain Variable Region of Chimeric Antibody (SEQ ID No. 57) | 0.89 |
| Light Chain Variable Region of Humanized Antibody (SEQ ID No. 14) | Heavy Chain Variable Region of Humanized Antibody (SEQ ID No. 13) | 0.34 |

| Heavy Chain AA residue 28 substitution | Light Chain AA | Mutant AA | Mutant AA classification | OD$_{450nm}$ (Peptide conc. 25 ng/mL) |
|---|---|---|---|---|
| S028F | Humanized (SEQ ID No. 14) | F | Hydrophobic | 0.16 |
| S028K | Humanized | K | Basic | 0.29 |
| S028R | Humanized | R | Basic | 0.60 |
| S028Y | Humanized | Y | Neutral | 0.17 |
| S028G | Humanized | G | Neutral | 0.06 |
| S028I | Humanized | I | Hydrophobic | 0.08 |
| S028L | Humanized | L | Hydrophobic | 0.10 |
| S028M | Humanized | M | Hydrophobic | 0.07 |
| S028Q | Humanized | Q | Neutral | 0.12 |
| S028W | Humanized | W | Hydrophobic | 0.11 |
| Chimeric (SEQ ID No. 57) | Chimeric (SEQ ID No. 58) | | | 0.13 |

FIGURE 4A

| Heavy Chain AA residue 31 substitution | Light Chain AA | Mutant AA | Mutant AA classification | OD$_{450nm}$ (Peptide conc. 25 ng/mL) |
|---|---|---|---|---|
| T031R | Humanized (SEQ ID No. 14) | R | Basic | 0.28 |
| T031D | Humanized | D | Acidic | 0.06 |
| T031E | Humanized | E | Acidic | 0.06 |
| T031G | Humanized | G | Neutral | 0.08 |
| T031H | Humanized | H | Basic | 0.10 |
| T031K | Humanized | K | Basic | 0.13 |
| T031L | Humanized | L | Hydrophobic | 0.09 |
| T031M | Humanized | M | Hydrophobic | 0.08 |
| T031Q | Humanized | Q | Neutral | 0.08 |
| T031S | Humanized | S | Neutral | 0.12 |
| Chimeric (SEQ ID No. 57) | Chimeric (SEQ ID No. 58) | | | 0.13 |

FIGURE 4B

| Heavy Chain AA residue 57 substitution | Light Chain | Mutant AA | Mutant AA classification | OD$_{450nm}$ (Peptide conc. 25 ng/mL) |
|---|---|---|---|---|
| D057G | Humanized (SEQ ID No. 14) | G | Neutral | 0.20 |
| D057H | Humanized | H | Basic | 0.15 |
| D057I | Humanized | I | Hydrophobic | 0.09 |
| D057N | Humanized | N | Neutral | 0.09 |
| D057P | Humanized | P | Hydrophobic | 0.07 |
| D057Q | Humanized | Q | Neutral | 0.12 |
| D057S | Humanized | S | Neutral | 0.15 |
| D057T | Humanized | T | Neutral | 0.08 |
| D057V | Humanized | V | Hydrophobic | 0.07 |
| D057W | Humanized | W | Hydrophobic | 0.15 |
| Chimeric (SEQ ID No. 57) | Chimeric (SEQ ID No. 58) | | | 0.11 |

FIGURE 4C

| Heavy Chain AA residue 63 substitution | Light Chain | Mutant AA | Mutant AA classification | OD$_{450nm}$ (Peptide conc. 25 ng/mL) |
|---|---|---|---|---|
| P063A | Humanized (SEQ ID No. 14) | A | Hydrophobic | 0.15 |
| P063L | Humanized | L | Hydrophobic | 0.17 |
| P063V | Humanized | V | Hydrophobic | 0.16 |
| P063Y | Humanized | Y | Neutral | 0.17 |
| P063H | Humanized | H | Basic | 0.13 |
| P063M | Humanized | M | Hydrophobic | 0.10 |
| P063N | Humanized | N | Neutral | 0.11 |
| P063Q | Humanized | Q | Neutral | 0.11 |
| P063R | Humanized | R | Basic | 0.12 |
| P063T | Humanized | T | Neutral | 0.11 |
| Chimeric (SEQ ID No. 57) | Chimeric (SEQ ID No. 58) | | | 0.11 |

FIGURE 4D

| Heavy Chain AA residue 105 substitution | Light Chain | Mutant AA | Mutant AA classification | OD$_{450nm}$ (Peptide conc. 25 ng/mL) |
|---|---|---|---|---|
| D105G | Humanized (SEQ ID No. 14) | G | Neutral | 0.15 |
| D105K | Humanized | K | Basic | 0.11 |
| D105M | Humanized | M | Hydrophobic | 0.12 |
| D105R | Humanized | R | Basic | 0.38 |
| D105A | Humanized | A | Hydrophobic | 0.10 |
| D105E | Humanized | E | Acidic | 0.08 |
| D105I | Humanized | I | Hydrophobic | 0.11 |
| D105L | Humanized | L | Hydrophobic | 0.09 |
| D105T | Humanized | T | Neutral | 0.10 |
| D105V | Humanized | V | Hydrophobic | 0.10 |
| Chimeric (SEQ ID No. 57) | Chimeric (SEQ ID No. 58) | | | 0.09 |

FIGURE 4E

| Light Chain AA residue 24 substitution | Heavy Chain | Mutant AA | Mutant aa classification | OD$_{450nm}$ (Peptide conc. 50 ng/mL) |
|---|---|---|---|---|
| R024G | Humanized (SEQ ID No. 13) | G | Neutral | 0.497 |
| R024H | Humanized | H | Basic | 0.354 |
| R024M | Humanized | M | Hydrophobic | 0.060 |
| R024N | Humanized | N | Neutral | 0.366 |
| R024P | Humanized | P | Hydrophobic | 0.209 |
| R024S | Humanized | S | Neutral | 0.871 |
| R024T | Humanized | T | Neutral | 0.247 |
| R024V | Humanized | V | Hydrophobic | 0.063 |
| R024W | Humanized | W | Hydrophobic | 0.512 |
| R024Y | Humanized | Y | Neutral | 0.300 |
| Chimeric (SEQ ID No. 58) | Chimeric (SEQ ID No. 57) | | | 0.388 |

FIGURE 5A

| Light Chain AA residue 32 substitution | Heavy Chain | Mutant AA | Mutant aa classification | OD$_{450nm}$ (Peptide conc. 50 ng/mL) |
|---|---|---|---|---|
| M032G | Humanized (SEQ ID No. 13) | G | Neutral | 0.516 |
| M032H | Humanized | H | Basic | 0.211 |
| M032K | Humanized | K | Basic | 0.251 |
| M032L | Humanized | L | Hydrophobic | 0.369 |
| M032Q | Humanized | Q | Neutral | 0.520 |
| M032R | Humanized | R | Basic | 0.061 |
| M032S | Humanized | S | Neutral | 0.064 |
| M032T | Humanized | T | Neutral | 0.306 |
| M032V | Humanized | V | Hydrophobic | 0.888 |
| M032W | Humanized | W | Hydrophobic | 0.364 |
| Chimeric (SEQ ID No. 58) | Chimeric (SEQ ID No. 57) | | | 0.396 |

FIGURE 5B

| Light Chain AA residue 49 substitution | Heavy Chain | Mutant AA | Mutant aa classification | OD$_{450nm}$ (Peptide conc. 50 ng/mL) |
|---|---|---|---|---|
| A049D | Humanized (SEQ ID No. 13) | D | Acidic | 0.060 |
| A049E | Humanized | E | Acidic | 0.065 |
| A049F | Humanized | F | Hydrophobic | 0.062 |
| A049G | Humanized | G | Neutral | 0.592 |
| A049K | Humanized | K | Basic | 0.061 |
| A049L | Humanized | L | Hydrophobic | 0.061 |
| A049M | Humanized | M | Hydrophobic | 0.061 |
| A049N | Humanized | N | Neutral | 0.063 |
| A049R | Humanized | R | Basic | 0.067 |
| A049T | Humanized | T | Neutral | 0.061 |
| Chimeric (SEQ ID No. 58) | Chimeric (SEQ ID No. 57) | | | 0.396 |

FIGURE 5C

| Light Chain AA residue 53 substitution | Heavy Chain | Mutant AA | Mutant aa classification | OD$_{450nm}$ (Peptide conc. 50 ng/mL) |
|---|---|---|---|---|
| L053D | Humanized (SEQ ID No. 13) | D | Acidic | 0.308 |
| L053E | Humanized | E | Acidic | 0.340 |
| L053G | Humanized | G | Neutral | 0.490 |
| L053K | Humanized | K | Basic | 0.532 |
| L053N | Humanized | N | Neutral | 0.102 |
| L053P | Humanized | P | Hydrophobic | 0.250 |
| L053R | Humanized | R | Basic | 0.348 |
| L053S | Humanized | S | Neutral | 0.305 |
| L053T | Humanized | T | Neutral | 0.401 |
| L053W | Humanized | W | Hydrophobic | 0.389 |
| Chimeric (SEQ ID No. 58) | Chimeric (SEQ ID No. 57) | | | 0.396 |

FIGURE 5D

| Light Chain AA residue 93 substitution | Heavy Chain | Mutant AA | Mutant aa classification | OD$_{450nm}$ (Peptide conc. 50 ng/mL) |
|---|---|---|---|---|
| N093E | Humanized (SEQ ID No. 13) | E | Acidic | 0.216 |
| N093F | Humanized | F | Hydrophobic | 0.455 |
| N093H | Humanized | H | Basic | 0.088 |
| N093L | Humanized | L | Hydrophobic | 0.426 |
| N093M | Humanized | M | Hydrophobic | 0.310 |
| N093Q | Humanized | Q | Neutral | 0.337 |
| N093R | Humanized | R | Basic | 0.375 |
| N093S | Humanized | S | Neutral | 0.316 |
| N093T | Humanized | T | Neutral | 0.346 |
| N093V | Humanized | V | Hydrophobic | 0.121 |
| Chimeric (SEQ ID No. 58) | Chimeric (SEQ ID No. 57) | | | 0.164 |

FIGURE 5E

| Light Chain Variable Region Amino Acid Substitutions | Heavy Chain Variable Region Amino Acid Substitutions | OD$_{450}$nm (peptide conc. 50 ng/mL) |
|---|---|---|
| A049G | S028R,T031R,D057G,P063Y,D105R | 3.09 |
| A049G,L053K,N093R | S028R,T031R,D105R | 3.04 |
| A049G,L053K,N093R | S028R,T031R,D057G,D105R | 3.00 |
| L053K,N093R | S028R,T031R,D105R | 3.00 |
| A049G,L053K,N093R | T031R,D105R | 2.99 |
| A049G,N093R | S028R,T031R,D105R | 2.99 |
| R024W,A049G,L053K,N093R | T031R,D057G,D105R | 2.98 |
| L053K,N093R | T031R,D105R | 2.94 |
| A049G | S028R,T031R,D105R | 2.92 |
| A049G,L053K,N093R | T031R,D057G,P063Y,D105R | 2.91 |
| A049G,N093R | S028R,T031R,D057G,D105R | 2.90 |
| L053K | S028R,T031R,D105R | 2.88 |
| L053K | S028R,T031R,D057G,P063Y,D105R | 2.82 |
| A049G,N093R | T031R,D105R | 2.81 |
| A049G,N093R | T031R,D057G,P063Y,D105R | 2.79 |
| A049G,L053K | S028R,T031R,D105R | 2.75 |
| A049G,L053K,N093R | S028R,T031R,P063Y | 2.73 |
| A049G,N093R | T031R,P063Y,D105R | 2.72 |
| A049G,L053K,N093R | T031R,P063Y,D105R | 2.72 |
| Humanized (SEQ ID No. 14) | S028R,T031R,D105R | 2.70 |
| A049G | T031R,D057G,P063Y,D105R | 2.69 |
| R024W,L053K,N093R | T031R,D057G,D105R | 2.69 |
| R024W,A049G,N093R | S028R,T031R,P063Y,D105R | 2.69 |
| A049G,L053K | 028R,T031R,D057G,P063Y,D105R | 2.68 |
| L053K,N093R | T031R,D057G,P063Y,D105R | 2.68 |

FIGURE 6

| | | |
|---|---|---|
| A049G,N093R | 028R,T031R,D057G,P063Y,D105R | 2.68 |
| Humanized (SEQ ID No. 14) | S028R,T031R,D057G,D105R | 2.66 |
| N093R | S028R,T031R,D105R | 2.65 |
| R024W,A049G,N093R | T031R,D057G,D105R | 2.65 |
| Humanized (SEQ ID No. 14) | S028R,T031R,P063Y | 2.64 |
| A049G,L053K,N093R | S028R,T031R,D057G,P063Y | 2.62 |
| L053K,N093R | S028R,T031R,D057G,D105R | 2.61 |
| Humanized (SEQ ID No. 14) | T031R,D057G,P063Y,D105R | 2.60 |
| Humanized (SEQ ID No. 14) | S028R,T031R,D057G,P063Y,D105R | 2.59 |
| M032Q,A049G,L053K,N093R | T031R,D057G,D105R | 2.59 |
| A049G,L053K | T031R,D057G,P063Y,D105R | 2.59 |
| A049G,L053K,N093R | S028R,T031R,D057G,P063Y,D105R | 2.58 |
| A049G,L053K,N093R | S028R,T031R,D057G | 2.57 |
| L053K,N093R | T031R,P063Y,D105R | 2.56 |
| A049G,L053K,N093R | S028R,D105R | 2.56 |
| L053K | S028R,T031R,D057G,D105R | 2.54 |
| M032Q,A049G,N093R | T031R,D057G,D105R | 2.54 |
| A049G,L053K | S028R,T031R,D057G,D105R | 2.53 |
| R024W,A049G,L053K,N093R | S028R,T031R,P063Y,D105R | 2.50 |
| Humanized (SEQ ID No. 14) | T031R,P063Y,D105R | 2.49 |
| L053K,N093R | S028R,T031R,D057G,P063Y | 2.47 |
| L053K | T031R,D057G,P063Y,D105R | 2.47 |
| N093R | S028R,T031R,D057G,P063Y,D105R | 2.46 |
| A049G,L053K,N093R | S028R,D057G,P063Y | 2.46 |
| L053K,N093R | S028R,T031R,D057G | 2.46 |
| N093R | S028R,T031R,D057G,P063Y | 2.45 |
| A049G,N093R | S028R,T031R,D057G,P063Y | 2.45 |
| R024W,A049G | S028R,T031R,D105R | 2.45 |
| N093R | S028R,T031R,D057G,D105R | 2.44 |
| L053K,N093R | S028R,D105R | 2.44 |

FIGURE 6 (CONT'D)

| | | |
|---|---|---|
| Humanized (SEQ ID No. 14) | S028R,T031R,D057G,P063Y | 2.37 |
| N093R | T031R,D057G,P063Y,D105R | 2.36 |
| R024W,A049G,L053K,N093R | T031R,D057G,P063Y | 2.35 |
| A049G,N093R | S028R,T031R,P063Y | 2.33 |
| A049G | S028R,T031R,D057G,P063Y | 2.32 |
| L053K | S028R,T031R,D057G,P063Y | 2.32 |
| A049G,L053K | T031R,P063Y,D105R | 2.31 |
| A049G,L053K,N093R | T031R,P063Y | 2.30 |
| R024W,A049G,N093R | T031R,P063Y,D105R | 2.29 |
| N093R | T031R,D105R | 2.29 |
| A049G,L053K | T031R,D105R | 2.28 |
| N093R | T031R,P063Y,D105R | 2.27 |
| R024W,A049G,N093R | S028R,T031R,D105R | 2.25 |
| L053K,N093R | S028R,T031R,D057G,P063Y,D105R | 2.24 |
| A049G | S028R,T031R,D057G,D105R | 2.21 |
| R024W,A049G,N093R | T031R,D105R | 2.19 |
| R024W | S028R,T031R,D057G,P063Y | 2.19 |
| N093R | S028R,D105R | 2.19 |
| N093R | S028R,T031R,P063Y | 2.18 |
| R024W,A049G | S028R,T031R,D057G,D105R | 2.18 |
| L053K,N093R | S028R,T031R,P063Y | 2.16 |
| M032Q,A049G,L053K,N093R | T031R,D057G,P063Y | 2.15 |
| A049G,L053K,N093R | S028R,P063Y | 2.14 |
| R024W,L053K,N093R | S028R,T031R,P063Y,D105R | 2.14 |
| R024W,A049G,L053K | S028R,T031R,P063Y | 2.13 |
| R024W,A049G,L053K,N093R | S028R,D057G,P063Y,D105R | 2.13 |
| R024W,A049G,L053K | S028R,T031R,D057G,P063Y | 2.12 |
| A049G,L053K | S028R,T031R,D057G,P063Y | 2.12 |
| R024W | S028R,T031R,D105R | 2.11 |
| Humanized (SEQ ID No. 14) | T031R,D105R | 2.10 |

FIGURE 6 (CONT'D)

| | | |
|---|---|---|
| R024W,A049G,N093R | S028R,D057G,P063Y,D105R | 2.10 |
| A049G,L053K | S028R,T031R,P063Y | 2.09 |
| R024W,A049G,N093R | T031R,D057G,P063Y | 2.09 |
| R024W,L053K,N093R | T031R,D105R | 2.08 |
| R024W,A049G | 028R,T031R,D057G,P063Y,D105R | 2.08 |
| R024W,A049G | T031R,D057G,P063Y,D105R | 2.08 |
| R024W,A049G,L053K | D057G,D105R | 2.08 |
| R024W,A049G,L053K | S028R,T031R,D105R | 2.08 |
| N093R | S028R,T031R,D057G | 2.07 |
| R024W,L053K,N093R | S028R,T031R,D105R | 2.07 |
| L053K | S028R,T031R,P063Y | 2.04 |
| A049G,N093R | S028R,D105R | 2.04 |
| R024W,A049G | T031R,P063Y,D105R | 2.04 |
| R024W,A049G,N093R | S028R,T031R,D057G,D105R | 2.01 |
| M032Q,A049G,N093R | T031R,D057G,P063Y | 2.01 |
| R024W,L053K,N093R | T031R,D057G,P063Y | 1.98 |
| R024W,A049G | T031R,D105R | 1.98 |
| R024W,L053K | S028R,T031R,D105R | 1.97 |
| R024W,A049G | S028R,T031R | 1.96 |
| A049G,N093R | S028R,T031R,D057G | 1.95 |
| R024W,A049G,L053K | D105R | 1.95 |
| R024W,A049G,N093R | S028R,T031R,D057G,P063Y | 1.95 |
| A049G | S028R,D057G,P063Y,D105R | 1.95 |
| R024W,M032Q,A049G,N093R | T031R,D057G,D105R | 1.94 |
| N093R | D057G,D105R | 1.93 |
| M032Q,N093R | T031R,D057G,D105R | 1.93 |
| R024W,A049G,L053K | T031R | 1.92 |
| R024W,A049G | D057G,P063Y,D105R | 1.92 |
| N093R | D057G,P063Y,D105R | 1.91 |
| N093R | T031R,D057G,D105R | 1.91 |

FIGURE 6 (CONT'D)

| | | |
|---|---|---|
| R024W,A049G,L053K,N093R | T031R,D105R | 1.90 |
| R024W,A049G,L053K | D057G,P063Y,D105R | 1.90 |
| R024W,A049G,L053K | S028R,D057G,P063Y | 1.90 |
| A049G,L053K,N093R | P063Y,D105R | 1.90 |
| R024W,A049G,L053K | P063Y,D105R | 1.90 |
| R024W,A049G,L053K,N093R | D057G,D105R | 1.90 |
| Humanized (SEQ ID No. 14) | S028R,T031R,P063Y,D105R | 1.89 |
| A049G,N093R | D057G,P063Y,D105R | 1.89 |
| R024W,L053K | S028R,T031R,D057G | 1.89 |
| A049G,L053K | D105R | 1.88 |
| R024W,L053K,N093R | D105R | 1.88 |
| R024W,A049G,L053K | S028R,T031R | 1.87 |
| R024W,A049G,N093R | T031R,D057G,P063Y,D105R | 1.87 |
| R024W,A049G,L053K | T031R,D057G,P063Y,D105R | 1.87 |
| Humanized (SEQ ID No. 14) | T031R,P063Y | 1.86 |
| A049G,L053K,N093R | T031R,D057G,D105R | 1.86 |
| R024W,A049G,N093R | S028R,D105R | 1.85 |
| R024W | S028R,T031R,D057G,D105R | 1.85 |
| L053K | T031R,P063Y,D105R | 1.85 |
| R024W,A049G,L053K,N093R | S028R,T031R,D105R | 1.84 |
| L053K,N093R | D057G,P063Y,D105R | 1.84 |
| R024W,A049G,L053K,N093R | D105R | 1.83 |
| Humanized (SEQ ID No. 14) | T031R,D057G,D105R | 1.83 |
| R024W,A049G | D057G,D105R | 1.82 |
| R024W,A049G,L053K,N093R | T031R | 1.81 |
| N093R | S028R,D057G,P063Y | 1.81 |
| A049G | T031R,D057G,D105R | 1.80 |
| R024W,A049G,N093R | S028R,T031R,P063Y | 1.80 |
| R024W,A049G,L053K,N093R | S028R,T031R | 1.80 |
| A049G,L053K,N093R | D057G,P063Y,D105R | 1.80 |

FIGURE 6 (CONT'D)

| | | |
|---|---|---|
| R024W,L053K | D057G,D105R | 1.79 |
| R024W,A049G,L053K,N093R | P063Y,D105R | 1.79 |
| R024W | S028R,T031R,D057G,P063Y,D105R | 1.79 |
| R024W,L053K,N093R | D057G,D105R | 1.78 |
| R024W,L053K | S028R,T031R | 1.77 |
| R024W,A049G | S028R,T031R,P063Y | 1.77 |
| L053K | D057G,D105R | 1.77 |
| R024W,A049G,L053K,N093R | S028R,T031R,D057G,D105R | 1.76 |
| A049G,N093R | D105R | 1.76 |
| A049G,N093R | S028R,D057G,P063Y | 1.75 |
| A049G,N093R | S028R,D057G,P063Y,D105R | 1.75 |
| R024W,A049G | T031R | 1.75 |
| A049G,N093R | P063Y,D105R | 1.75 |
| A049G,L053K | S028R,T031R | 1.75 |
| L053K | T031R,D057G,D105R | 1.74 |
| N093R | T031R,D057G,P063Y | 1.74 |
| R024W,A049G,N093R | D057G,P063Y,D105R | 1.74 |
| A049G,N093R | T031R,D057G,D105R | 1.74 |
| M032Q,A049G,L053K,N093R | T031R,D105R | 1.73 |
| M032Q,A049G,L053K | T031R | 1.73 |
| R024W,L053K | D105R | 1.73 |
| A049G | S028R,T031R | 1.73 |
| A049G,L053K,N093R | S028R,T031R | 1.72 |
| R024W,L053K,N093R | D057G,P063Y,D105R | 1.71 |
| R024W,A049G | S028R,T031R,D057G,P063Y | 1.71 |
| A049G,L053K | P063Y,D105R | 1.70 |
| A049G,L053K | D057G,D105R | 1.70 |
| R024W,A049G,L053K,N093R | S028R,D105R | 1.70 |
| R024W,A049G,N093R | S028R,T031R,D057G | 1.70 |
| N093R | D105R | 1.70 |

FIGURE 6 (CONT'D)

| | | |
|---|---|---|
| M032Q,A049G,L053K,N093R | D105R | 1.69 |
| R024W,A049G,L053K | S028R | 1.69 |
| Humanized (SEQ ID No. 14) | S028R,T031R,D057G | 1.69 |
| R024W,L053K,N093R | P063Y,D105R | 1.69 |
| A049G,L053K,N093R | D105R | 1.68 |
| A049G | P063Y,D105R | 1.68 |
| R024W,A049G,L053K,N093R | S028R | 1.68 |
| A049G,L053K | S028R,D057G,P063Y,D105R | 1.67 |
| R024W,A049G,L053K,N093R | S028R,T031R,D057G | 1.66 |
| R024W,A049G,L053K | 028R,T031R,D057G,P063Y,D105R | 1.65 |
| A049G,N093R | T031R,D057G,P063Y | 1.65 |
| N093R | S028R,D057G,P063Y,D105R | 1.64 |
| Humanized (SEQ ID No. 14) | S028R,D057G,P063Y,D105R | 1.64 |
| A049G,L053K,N093R | T031R,D057G,P063Y | 1.64 |
| A049G,L053K | D057G,P063Y,D105R | 1.64 |
| L053K,N093R | T031R,D057G,D105R | 1.64 |
| R024W,A049G | P063Y,D105R | 1.63 |
| A049G,L053K | T031R,D057G,D105R | 1.63 |
| Humanized (SEQ ID No. 14) | S028R,D105R | 1.63 |
| R024W,L053K,N093R | S028R,T031R,D057G,D105R | 1.62 |
| L053K | D057G,P063Y,D105R | 1.62 |
| R024W,A049G,L053K,N093R | D057G | 1.62 |
| A049G,N093R | D057G,D105R | 1.62 |
| M032Q,A049G,N093R | D105R | 1.62 |
| A049G,N093R | S028R,T031R | 1.60 |
| N093R | S028R,T031R | 1.60 |
| R024W,A049G,L053K | T031R,D105R | 1.60 |
| A049G | S028R,T031R,P063Y,D105R | 1.60 |
| R024W,A049G,L053K | S028R,T031R,D057G,D105R | 1.60 |
| R024W,A049G,L053K | T031R,P063Y,D105R | 1.60 |

FIGURE 6 (CONT'D)

| | | |
|---|---|---|
| M032Q,A049G,L053K | T031R,D105R | 1.59 |
| R024W,A049G,L053K,N093R | T031R,P063Y,D105R | 1.59 |
| L053K,N093R | D105R | 1.58 |
| L053K | S028R,T031R | 1.58 |
| M032Q,A049G | S028R,T031R,D105R | 1.58 |
| R024W,L053K | S028R,T031R,D057G,D105R | 1.58 |
| R024W,A049G,L053K,N093R | D057G,P063Y,D105R | 1.58 |
| A049G,L053K,N093R | T031R | 1.58 |
| A049G | T031R,D057G,P063Y | 1.58 |
| R024W,A049G,L053K | S028R,D105R | 1.58 |
| R024W,A049G,L053K | D057G | 1.57 |
| R024W,A049G,L053K | T031R,P063Y | 1.57 |
| M032Q,A049G,L053K,N093R | T031R | 1.55 |
| A049G | D057G,D105R | 1.55 |
| Humanized (SEQ ID No. 14) | T031R,D057G,P063Y | 1.55 |
| N093R | T031R,P063Y | 1.55 |
| R024W,A049G | D105R | 1.55 |
| A049G,N093R | T031R,P063Y | 1.54 |
| M032Q,A049G,L053K | S028R | 1.54 |
| R024W,A049G,N093R | S028R,D057G,P063Y | 1.54 |
| L053K,N093R | D057G,D105R | 1.53 |
| M032Q,L053K,N093R | D105R | 1.53 |
| Humanized (SEQ ID No. 14) | S028R,D057G,P063Y | 1.53 |
| N093R | S028R,T031R,P063Y,D105R | 1.53 |
| R024W,A049G,N093R | S028R,T031R | 1.53 |
| L053K,N093R | T031R,P063Y | 1.52 |
| L053K,N093R | P063Y,D105R | 1.52 |
| L053K | D105R | 1.52 |
| R024W,A049G,N093R | T031R | 1.52 |
| R024W,L053K,N093R | S028R,D057G,P063Y,D105R | 1.52 |

FIGURE 6 (CONT'D)

| | | |
|---|---|---|
| R024W,A049G | S028R | 1.51 |
| Humanized (SEQ ID No. 14) | P063Y,D105R | 1.51 |
| M032Q,A049G,N093R | T031R,D105R | 1.51 |
| A049G | D105R | 1.50 |
| A049G,L053K | T031R,D057G,P063Y | 1.49 |
| L053K | P063Y,D105R | 1.49 |
| A049G | D057G,P063Y,D105R | 1.48 |
| R024W | S028R,T031R,P063Y | 1.47 |
| R024W,A049G | T031R,D057G,D105R | 1.47 |
| R024W,A049G,L053K | Humanized (SEQ ID No. 13) | 1.47 |
| L053K,N093R | S028R,D057G,P063Y | 1.47 |
| R024W,L053K | T031R | 1.46 |
| A049G,L053K | S028R,D057G,P063Y | 1.46 |
| A049G | T031R,D105R | 1.46 |
| R024W,M032Q,A049G,N093R | D105R | 1.46 |
| L053K,N093R | S028R,T031R | 1.46 |
| A049G,L053K | S028R,D105R | 1.45 |
| M032Q,A049G,L053K,N093R | D057G | 1.44 |
| Humanized (SEQ ID No. 14) | S028R,T031R | 1.44 |
| Humanized (SEQ ID No. 14) | S028R,P063Y | 1.44 |
| N093R | P063Y,D105R | 1.43 |
| L053K | T031R,D057G,P063Y | 1.43 |
| R024W,A049G,N093R | D057G | 1.43 |
| M032Q,A049G,L053K | D105R | 1.42 |
| R024W,L053K,N093R | T031R,P063Y,D105R | 1.42 |
| M032Q,A049G,L053K | S028R,T031R,D057G,P063Y | 1.41 |
| M032Q,A049G,N093R | D057G,D105R | 1.41 |
| M032Q,L053K | T031R | 1.41 |
| M032Q,A049G,N093R | S028R,T031R,P063Y,D105R | 1.41 |
| R024W,L053K | P063Y,D105R | 1.41 |

FIGURE 6 (CONT'D)

| | | |
|---|---|---|
| L053K | T031R,D105R | 1.41 |
| R024W,A049G | D057G | 1.41 |
| M032Q,A049G,L053K,N093R | S028R | 1.40 |
| L053K | S028R,D105R | 1.40 |
| R024W,A049G,N093R | D057G,D105R | 1.40 |
| A049G,N093R | S028R,T031R,P063Y,D105R | 1.39 |
| R024W,L053K | S028R,T031R,P063Y | 1.38 |
| L053K,N093R | T031R | 1.38 |
| A049G | T031R,P063Y,D105R | 1.38 |
| A049G,N093R | S028R,P063Y | 1.38 |
| A049G,L053K | S028R,T031R,P063Y,D105R | 1.37 |
| R024W,L053K | D057G,P063Y,D105R | 1.35 |
| L053K,N093R | S028R,P063Y | 1.35 |
| R024W,A049G,L053K,N093R | T031R,D057G,P063Y,D105R | 1.33 |
| M032Q,A049G,L053K,N093R | S028R,D105R | 1.33 |
| A049G | S028R,D105R | 1.32 |
| R024W,M032Q,A049G,N093R | T031R,D105R | 1.32 |
| R024W,A049G,L053K,N093R | S028R,T031R,D057G,P063Y | 1.32 |
| R024W,A049G,L053K,N093R | T031R,P063Y | 1.31 |
| R024W,A049G,N093R | P063Y,D105R | 1.31 |
| R024W,A049G,L053K,N093R | P063Y | 1.31 |
| R024W,A049G,N093R | S028R | 1.31 |
| M032Q,A049G | D105R | 1.31 |
| R024W,A049G,N093R | T031R,P063Y | 1.31 |
| R024W,L053K | T031R,D105R | 1.30 |
| R024W,A049G,L053K,N093R | S028R,D057G,P063Y | 1.30 |
| R024W,A049G,L053K | S028R,P063Y | 1.30 |
| L053K | S028R,T031R,P063Y,D105R | 1.29 |
| R024W,L053K | T031R,P063Y,D105R | 1.29 |
| M032Q,A049G | D057G,D105R | 1.29 |

FIGURE 6 (CONT'D)

| | | |
|---|---|---|
| R024W,A049G,N093R | 028R,T031R,D057G,P063Y,D105R | 1.28 |
| A049G,L053K,N093R | S028R,D057G,P063Y,D105R | 1.28 |
| Humanized (SEQ ID No. 14) | D057G,P063Y,D105R | 1.26 |
| A049G,N093R | T031R | 1.26 |
| R024W,A049G,L053K,N093R | Humanized (SEQ ID No. 13) | 1.26 |
| R024W,L053K,N093R | T031R | 1.26 |
| R024W,A049G | S028R,T031R,D057G | 1.26 |
| M032Q,A049G,L053K | Humanized (SEQ ID No. 13) | 1.26 |
| R024W | S028R,D105R | 1.25 |
| M032Q,A049G,L053K | D057G | 1.25 |
| A049G,L053K | T031R,P063Y | 1.25 |
| M032Q,L053K | S028R,T031R | 1.24 |
| A049G,N093R | S028K | 1.24 |
| M032Q,A049G,N093R | S028R,D057G,P063Y,D105R | 1.23 |
| M032Q,N093R | D105R | 1.23 |
| M032Q,N093R | T031R,D057G,P063Y | 1.23 |
| A049G | S028R,T031R,P063Y | 1.22 |
| M032Q,A049G | T031R,D105R | 1.22 |
| R024W,L053K,N093R | S028R,T031R,D057G | 1.22 |
| M032Q,L053K,N093R | T031R,D105R | 1.21 |
| M032Q,L053K | S028R | 1.21 |
| R024W,L053K,N093R | S028R,D105R | 1.21 |
| M032Q,L053K | D057G | 1.20 |
| M032Q,A049G | S028R,T031R,D057G | 1.20 |
| A049G,L053K,N093R | S028R | 1.19 |
| M032Q,A049G | S028R | 1.19 |
| M032Q,N093R | T031R,D105R | 1.19 |
| A049G,L053K,N093R | S028R,T031R,P063Y,D105R | 1.18 |
| R024W | T031R,P063Y,D105R | 1.18 |
| M032Q,A049G,L053K | S028R,T031R,D105R | 1.18 |

FIGURE 6 (CONT'D)

| | | |
|---|---|---|
| M032Q,N093R | S028R,T031R,D057G | 1.18 |
| R024W,A049G,N093R | D105R | 1.17 |
| R024W | S028R,T031R | 1.17 |
| R024W,L053K | S028R | 1.17 |
| M032Q,A049G | S028R,T031R | 1.17 |
| M032Q,A049G | T031R | 1.16 |
| R024W,A049G | S028R,D057G,P063Y | 1.16 |
| M032Q,A049G | S028R,T031R,D057G,D105R | 1.15 |
| R024W,L053K,N093R | D057G | 1.15 |
| R024W,M032Q,A049G,N093R | D057G,D105R | 1.15 |
| M032Q,A049G | D057G,P063Y,D105R | 1.14 |
| R024W,A049G | T031R,D057G,P063Y | 1.14 |
| R024W,A049G,L053K | S028R,T031R,D057G | 1.14 |
| M032Q,A049G,N093R | S028R,T031R,D105R | 1.14 |
| A049G,L053K,N093R | D057G,D105R | 1.14 |
| R024W,L053K,N093R | S028R | 1.14 |
| R024W,A049G,L053K | P063Y | 1.14 |
| R024W,L053K | D057G | 1.13 |
| M032Q,A049G,N093R | D057G,P063Y,D105R | 1.13 |
| M032Q,A049G,N093R | T031R,P063Y,D105R | 1.12 |
| R024W | T031R,D057G,P063Y,D105R | 1.12 |
| A049G,L053K | T031R | 1.12 |
| M032Q,A049G,L053K,N093R | D057G,D105R | 1.11 |
| R024W,L053K,N093R | S028R,T031R | 1.11 |
| R024W,L053K,N093R | Humanized (SEQ ID No. 13) | 1.10 |
| 024W,M032Q,A049G,L053K,N093R | T031R,D105R | 1.10 |
| N093R | S028R,P063Y | 1.10 |
| L053K | S028R,T031R,D057G | 1.09 |
| A049G,L053K | S028R | 1.09 |
| N093R | T031R | 1.09 |

FIGURE 6 (CONT'D)

| | | |
|---|---|---|
| M032Q,A049G,L053K,N093R | S028R,T031R,D105R | 1.08 |
| L053K | T031R,P063Y | 1.07 |
| M032Q,N093R | S028R,T031R,D105R | 1.07 |
| 024W,M032Q,A049G,L053K,N093R | D105R | 1.07 |
| R024W,L053K | T031R,P063Y | 1.07 |
| R024W,A049G | T031R,P063Y | 1.07 |
| M032Q,A049G,N093R | S028R,T031R,D057G,D105R | 1.07 |
| A049G,L053K,N093R | D057G | 1.06 |
| R024W,A049G,L053K,N093R | S028R,P063Y | 1.05 |
| R024W,L053K | S028R,D057G,P063Y | 1.05 |
| M032Q,A049G | D057G | 1.05 |
| Humanized (SEQ ID No. 14) | D057G,D105R | 1.05 |
| M032Q,A049G,L053K | S028R,T031R | 1.04 |
| L053K,N093R | S028R,D057G,P063Y,D105R | 1.04 |
| M032Q,A049G,L053K,N093R | S028R,T031R,D057G | 1.04 |
| M032Q,A049G,L053K | S028R,D057G,P063Y | 1.04 |
| M032Q,A049G,N093R | S028R | 1.03 |
| M032Q,L053K,N093R | D057G,D105R | 1.02 |
| R024W,A049G | S028R,P063Y | 1.01 |
| L053K,N093R | S028R | 1.01 |
| M032Q,A049G,L053K,N093R | S028R,T031R,P063Y,D105R | 1.01 |
| M032Q,A049G | P063Y,D105R | 1.01 |
| M032Q,A049G | T031R,D057G,P063Y,D105R | 1.01 |
| L053K | T031R | 1.01 |
| M032Q,N093R | D057G,D105R | 1.00 |
| R024W,A049G,L053K,N093R | S028R,T031R,P063Y | 1.00 |
| R024W,A049G,N093R | S028R,P063Y | 1.00 |
| M032Q,L053K,N093R | S028R,D105R | 0.99 |
| A049G,N093R | D057G | 0.99 |
| M032Q,L053K,N093R | D057G | 0.99 |

FIGURE 6 (CONT'D)

| | | |
|---|---|---|
| L053K,N093R | T031R,D057G,P063Y | 0.99 |
| M032Q,A049G,L053K,N093R | S028R,T031R | 0.99 |
| M032Q,A049G,L053K | T031R,P063Y | 0.98 |
| R024W | D057G,D105R | 0.98 |
| M032Q,A049G,L053K | D057G,D105R | 0.98 |
| M032Q,L053K | D105R | 0.98 |
| 024W,M032Q,A049G,L053K,N093R | D057G | 0.98 |
| R024W | D057G,P063Y,D105R | 0.98 |
| M032Q,L053K,N093R | S028R | 0.97 |
| R024W | T031R,D057G,D105R | 0.97 |
| M032Q,A049G,N093R | P063Y,D105R | 0.97 |
| R024W,L053K | T031R,D057G,P063Y,D105R | 0.97 |
| M032Q,A049G,N093R | S028R,D105R | 0.97 |
| A049G | S028R | 0.96 |
| R024W,A049G | S028R,T031R,P063Y,D105R | 0.96 |
| M032Q,L053K | D057G,D105R | 0.95 |
| R024W,A049G,N093R | P063Y | 0.95 |
| M032Q,A049G,N093R | T031R | 0.94 |
| M032Q,A049G,L053K | S028R,D105R | 0.94 |
| L053K,N093R | D057G | 0.94 |
| R024W | T031R,D105R | 0.94 |
| R024W,L053K | S028R,P063Y | 0.93 |
| Humanized (SEQ ID No. 14) | T031R | 0.92 |
| A049G,L053K | D057G | 0.92 |
| R024W,L053K,N093R | T031R,D057G,P063Y,D105R | 0.92 |
| M032Q,A049G | S028R,T031R,D057G,P063Y | 0.92 |
| A049G,L053K | S028R,T031R,D057G | 0.92 |
| M032Q,L053K,N093R | T031R | 0.92 |
| R024W,M032Q,N093R | D105R | 0.92 |
| M032Q,A049G,L053K,N093R | Humanized (SEQ ID No. 13) | 0.91 |

FIGURE 6 (CONT'D)

| | | |
|---|---|---|
| M032Q,N093R | S028R,T031R,D057G,P063Y | 0.91 |
| M032Q,A049G | T031R,P063Y,D105R | 0.91 |
| R024W,M032Q,L053K | D057G | 0.91 |
| A049G | T031R | 0.91 |
| R024W,L053K | Humanized (SEQ ID No. 13) | 0.90 |
| R024W,M032Q,L053K | T031R | 0.89 |
| M032Q,A049G,L053K | S028R,T031R,D057G | 0.89 |
| M032Q,A049G,L053K,N093R | P063Y,D105R | 0.89 |
| R024W,A049G | P063Y | 0.88 |
| 024W,M032Q,A049G,L053K,N093R | T031R | 0.88 |
| M032Q,A049G,N093R | S028R,T031R,D057G | 0.87 |
| Humanized (SEQ ID No. 14) | D105R | 0.87 |
| L053K | S028R,D057G,P063Y,D105R | 0.87 |
| R024W,L053K,N093R | T031R,P063Y | 0.87 |
| A049G,L053K,N093R | P063Y | 0.87 |
| M032Q,A049G,N093R | D057G | 0.86 |
| M032Q,L053K,N093R | S028R,T031R,D057G | 0.86 |
| M032Q,A049G,L053K | D057G,P063Y,D105R | 0.86 |
| N093R | S028R | 0.85 |
| A049G,N093R | T031R,D057G | 0.85 |
| A049G,L053K,N093R | Humanized (SEQ ID No. 13) | 0.84 |
| R024W | S028R,T031R,D057G | 0.84 |
| M032Q,A049G,N093R | S028R,T031R | 0.84 |
| L053K,N093R | Humanized (SEQ ID No. 13) | 0.84 |
| A049G,N093R | D057G,P063Y | 0.84 |
| A049G,L053K | S028R,P063Y | 0.84 |
| M032Q,L053K | S028R,T031R,D057G | 0.83 |
| A049G | S028R,D057G,P063Y | 0.83 |
| A049G,L053K,N093R | D057G,P063Y | 0.83 |
| M032Q,L053K,N093R | Humanized (SEQ ID No. 13) | 0.82 |

FIGURE 6 (CONT'D)

| | | |
|---|---|---|
| M032Q,A049G | S028R,D057G,P063Y | 0.82 |
| L053K | S028R,D057G,P063Y | 0.82 |
| R024W,L053K,N093R | S028R,T031R,D057G,P063Y | 0.81 |
| M032Q,N093R | D057G,P063Y,D105R | 0.81 |
| R024W | S028R,T031R,P063Y,D105R | 0.81 |
| 024W,M032Q,A049G,L053K,N093R | S028R,T031R,D057G | 0.81 |
| R024W,L053K | T031R,D057G,D105R | 0.81 |
| M032Q,A049G,N093R | S028R,D057G,P063Y | 0.81 |
| N093R | D057G | 0.81 |
| M032Q,N093R | T031R | 0.80 |
| M032Q,A049G,L053K,N093R | T031R,P063Y,D105R | 0.80 |
| L053K | D057G | 0.80 |
| M032Q,A049G,L053K | S028R,T031R,P063Y | 0.80 |
| M032Q,A049G,L053K,N093R | S028R,T031R,D057G,D105R | 0.80 |
| L053K,N093R | S028R,T031R,P063Y,D105R | 0.79 |
| M032Q,A049G,N093R | T031R,P063Y | 0.79 |
| R024W,A049G,L053K | T031R,D057G,D105R | 0.79 |
| M032Q,A049G,L053K | P063Y,D105R | 0.79 |
| R024W,M032Q,A049G,N093R | S028R,T031R,D057G | 0.79 |
| A049G,L053K,N093R | T031R,D057G | 0.79 |
| R024W,L053K | P063Y | 0.78 |
| R024W | P063Y,D105R | 0.78 |
| M032Q,A049G | Humanized (SEQ ID No. 13) | 0.77 |
| M032Q,A049G,N093R | S028R,T031R,D057G,P063Y | 0.77 |
| A049G | D057G | 0.77 |
| R024W,M032Q,A049G,N093R | T031R | 0.77 |
| L053K | S028R | 0.77 |
| R024W,M032Q,A049G,N093R | D057G | 0.77 |
| R024W,L053K,N093R | S028R,T031R,P063Y | 0.76 |
| M032Q,N093R | S028R,T031R,P063Y,D105R | 0.76 |

FIGURE 6 (CONT'D)

| | | |
|---|---|---|
| 024W,M032Q,A049G,L053K,N093R | S028R,D105R | 0.76 |
| R024W,M032Q,L053K | S028R | 0.75 |
| R024W,L053K | T031R,D057G,P063Y | 0.75 |
| M032Q,A049G | T031R,P063Y | 0.75 |
| R024W | T031R | 0.75 |
| M032Q,A049G,N093R | S028R,T031R,P063Y | 0.75 |
| R024W,L053K,N093R | S028R,P063Y | 0.74 |
| M032Q,A049G | S028R,T031R,P063Y | 0.74 |
| L053K,N093R | D057G,P063Y | 0.73 |
| R024W,M032Q,N093R | D057G | 0.73 |
| R024W,M032Q,A049G,N093R | S028R,D105R | 0.72 |
| M032Q,A049G,L053K,N093R | S028R,D057G,P063Y,D105R | 0.72 |
| A049G,N093R | Humanized (SEQ ID No. 13) | 0.71 |
| A049G,N093R | P063Y | 0.71 |
| M032Q,N093R | S028R,T031R,D057G,D105R | 0.71 |
| M032Q,A049G | P063Y | 0.71 |
| R024W,A049G | Humanized (SEQ ID No. 13) | 0.70 |
| R024W,A049G,L053K,N093R | S028R,T031R,D057G,P063Y,D105R | 0.70 |
| M032Q,N093R | P063Y,D105R | 0.70 |
| 024W,M032Q,A049G,L053K,N093R | S028R | 0.70 |
| R024W,L053K | S028R,T031R,D057G,P063Y | 0.69 |
| L053K | S028R,P063Y | 0.69 |
| M032Q,A049G,L053K,N093R | P063Y | 0.69 |
| L053K,N093R | P063Y | 0.69 |
| R024W,L053K,N093R | P063Y | 0.68 |
| A049G,L053K | P063Y | 0.68 |
| R024W | T031R,P063Y | 0.68 |
| M032Q,A049G | T031R,D057G,P063Y | 0.68 |
| 024W,M032Q,A049G,L053K,N093R | Humanized (SEQ ID No. 13) | 0.66 |
| R024W,L053K,N093R | S028R,D057G,P063Y | 0.66 |

FIGURE 6 (CONT'D)

| | | |
|---|---|---|
| M032Q,N093R | S028R,D057G,P063Y | 0.66 |
| M032Q,N093R | D057G | 0.65 |
| A049G,L053K | Humanized (SEQ ID No. 13) | 0.65 |
| M032Q,L053K | Humanized (SEQ ID No. 13) | 0.65 |
| R024W,M032Q,L053K,N093R | D057G | 0.64 |
| Humanized (SEQ ID No. 14) | S028R | 0.64 |
| M032Q,A049G | 028R,T031R,D057G,P063Y,D105R | 0.64 |
| M032Q,A049G,L053K,N093R | T031R,P063Y | 0.63 |
| M032Q,A049G,N093R | T031R,D057G,P063Y,D105R | 0.63 |
| R024W,M032Q,N093R | S028R,T031R,D057G | 0.61 |
| R024W,M032Q,A049G,N093R | S028R,T031R,D105R | 0.60 |
| R024W,M032Q,L053K | Humanized (SEQ ID No. 13) | 0.60 |
| R024W,A049G | S028R,D105R | 0.59 |
| M032Q,L053K,N093R | S028R,T031R,D105R | 0.59 |
| M032Q,A049G,L053K | S028R,T031R,D057G,D105R | 0.59 |
| R024W,A049G,L053K | T031R,D057G,P063Y | 0.58 |
| M032Q,A049G,L053K | S028R,P063Y | 0.58 |
| M032Q,A049G,L053K,N093R | S028R,D057G,P063Y | 0.58 |
| R024W,A049G | S028R,D057G,P063Y,D105R | 0.58 |
| N093R | Humanized (SEQ ID No. 13) | 0.58 |
| R024W,M032Q,A049G,N093R | P063Y,D105R | 0.58 |
| R024W | S028R | 0.58 |
| M032Q,L053K | P063Y | 0.57 |
| 024W,M032Q,A049G,L053K,N093R | S028R,T031R | 0.57 |
| M032Q,L053K,N093R | S028R,T031R | 0.57 |
| Humanized (SEQ ID No. 14) | D057G | 0.56 |
| M032Q,L053K,N093R | P063Y,D105R | 0.56 |
| R024W,M032Q,A049G,N093R | T031R,D057G,P063Y | 0.56 |
| A049G | Humanized (SEQ ID No. 13) | 0.56 |
| R024W,M032Q,A049G,L053K,N093R | T031R,D057G,D105R | 0.56 |

FIGURE 6 (CONT'D)

| | | |
|---|---|---|
| N093R | P063Y | 0.56 |
| R024W | S028R,D057G,P063Y | 0.55 |
| A049G | P063Y | 0.55 |
| M032Q,L053K | D057G,P063Y,D105R | 0.55 |
| R024W,A049G,L053K | D057G,P063Y | 0.54 |
| M032Q,A049G | T031R,D057G,D105R | 0.54 |
| R024W,M032Q,L053K | S028R,T031R | 0.53 |
| M032Q,L053K | P063Y,D105R | 0.53 |
| R024W,M032Q,A049G,N093R | S028R,T031R | 0.52 |
| M032Q,L053K,N093R | D057G,P063Y,D105R | 0.52 |
| R024W | T031R,D057G,P063Y | 0.52 |
| R024W | D105R | 0.52 |
| A049G,L053K | D057G,P063Y | 0.52 |
| M032Q,L053K | S028R,T031R,D057G,D105R | 0.51 |
| L053K | Humanized (SEQ ID No. 13) | 0.51 |
| N093R | T031R,D057G | 0.51 |
| L053K,N093R | T031R,D057G | 0.51 |
| M032Q,A049G,L053K | T031R,D057G,P063Y,D105R | 0.50 |
| R024W,L053K | S028R,D105R | 0.50 |
| R024W,L053K,N093R | 028R,T031R,D057G,P063Y,D105R | 0.50 |
| R024W,L053K | 028R,T031R,D057G,P063Y,D105R | 0.50 |
| M032Q,A049G | S028R,P063Y | 0.49 |
| R024W,M032Q,L053K | D105R | 0.48 |
| M032Q,N093R | S028R,T031R | 0.48 |
| M032Q,N093R | T031R,P063Y | 0.47 |
| M032Q | S028R,T031R,D105R | 0.47 |
| M032Q,A049G,L053K | P063Y | 0.47 |
| M032Q,A049G,L053K,N093R | T031R,D057G,P063Y,D105R | 0.46 |
| M032Q | T031R | 0.46 |
| R024W,M032Q,L053K,N093R | Humanized (SEQ ID No. 13) | 0.46 |

FIGURE 6 (CONT'D)

| | | |
|---|---|---|
| 024W,M032Q,A049G,L053K,N093R | D057G,D105R | 0.46 |
| M032Q | S028R,T031R,D057G | 0.45 |
| R024W,A049G,N093R | D057G,P063Y | 0.45 |
| M032Q,N093R | T031R,P063Y,D105R | 0.45 |
| R024W,M032Q,N093R | D057G,D105R | 0.45 |
| M032Q,A049G,L053K,N093R | S028R,T031R,D057G,P063Y | 0.44 |
| R024W,A049G,L053K | S028R,T031R,P063Y,D105R | 0.44 |
| R024W,M032Q,A049G,N093R | S028R | 0.44 |
| M032Q,A049G,L053K | S028R,T031R,D057G,P063Y,D105R | 0.43 |
| A049G | S028R,T031R,D057G | 0.43 |
| L053K | P063Y | 0.42 |
| M032Q,L053K,N093R | T031R,P063Y | 0.42 |
| A049G,L053K | T031R,D057G | 0.42 |
| M032Q,N093R | T031R,D057G,P063Y,D105R | 0.42 |
| R024W,M032Q,N093R | T031R,D105R | 0.41 |
| M032Q,A049G,N093R | Humanized (SEQ ID No. 13) | 0.41 |
| R024W,M032Q,N093R | T031R,D057G,D105R | 0.41 |
| M032Q,L053K | T031R,D105R | 0.41 |
| M032Q,A049G,L053K,N093R | S028R,P063Y | 0.41 |
| M032Q,A049G,L053K | T031R,P063Y,D105R | 0.41 |
| M032Q,N093R | S028R,D057G,P063Y,D105R | 0.41 |
| M032Q,N093R | S028R,T031R,P063Y | 0.41 |
| R024W,M032Q,A049G,N093R | D057G,P063Y,D105R | 0.40 |
| M032Q,L053K | S028R,T031R,D105R | 0.40 |
| M032Q | S028R,T031R,D057G,D105R | 0.40 |
| M032Q | S028R,T031R | 0.39 |
| M032Q,L053K | T031R,P063Y | 0.39 |
| M032Q,A049G,L053K,N093R | D057G,P063Y,D105R | 0.39 |
| R024W,M032Q,A049G,N093R | S028R,T031R,D057G,D105R | 0.39 |
| M032Q,L053K,N093R | P063Y | 0.39 |

FIGURE 6 (CONT'D)

| | | |
|---|---|---|
| R024W,M032Q,N093R | S028R,D105R | 0.39 |
| M032Q,L053K,N093R | S028R,D057G,P063Y | 0.38 |
| M032Q | D057G | 0.38 |
| R024W | P063Y | 0.38 |
| M032Q,L053K,N093R | S028R,T031R,D057G,P063Y | 0.37 |
| R024W,A049G,L053K | S028R,D057G,P063Y,D105R | 0.37 |
| M032Q | Humanized (SEQ ID No. 13) | 0.37 |
| M032Q,A049G,L053K | T031R,D057G,P063Y | 0.37 |
| R024W,M032Q,L053K,N093R | T031R | 0.37 |
| R024W,L053K | S028R,T031R,P063Y,D105R | 0.37 |
| R024W,M032Q,A049G,N093R | T031R,P063Y | 0.37 |
| Humanized (SEQ ID No. 14) | T031R,D057G | 0.36 |
| R024W,M032Q | T031R | 0.36 |
| A049G | T031R,P063Y | 0.36 |
| M032Q | S028R,T031R,D057G,P063Y | 0.36 |
| A049G | D057G,P063Y | 0.36 |
| R024W,M032Q,L053K,N093R | S028R | 0.35 |
| R024W,M032Q,L053K | S028R,T031R,D057G | 0.35 |
| R024W,M032Q,A049G,N093R | Humanized (SEQ ID No. 13) | 0.35 |
| M032Q,A049G,L053K | T031R,D057G,D105R | 0.35 |
| M032Q,L053K,N093R | S028R,T031R,D057G,D105R | 0.35 |
| Humanized (SEQ ID No. 14) | P063Y | 0.34 |
| R024W | S028R,P063Y | 0.34 |
| R024W | D057G | 0.34 |
| R024W,A049G,L053K,N093R | D057G,P063Y | 0.34 |
| R024W | Humanized (SEQ ID No. 13) | 0.34 |
| R024W,M032Q,A049G,N093R | S028R,T031R,P063Y,D105R | 0.34 |
| M032Q,A049G,N093R | P063Y | 0.34 |
| R024W,M032Q,A049G,N093R | T031R,P063Y,D105R | 0.33 |
| 024W,M032Q,A049G,L053K,N093R | T031R,D057G,P063Y | 0.33 |

FIGURE 6 (CONT'D)

| | | |
|---|---|---|
| R024W,A049G,N093R | Humanized (SEQ ID No. 13) | 0.33 |
| M032Q,N093R | S028R,P063Y | 0.33 |
| M032Q,A049G,L053K,N093R | S028R,T031R,P063Y | 0.33 |
| M032Q | T031R,D057G,P063Y | 0.32 |
| R024W,M032Q,N093R | S028R,T031R | 0.32 |
| L053K | D057G,P063Y | 0.32 |
| R024W | S028R,D057G,P063Y,D105R | 0.31 |
| M032Q,L053K,N093R | S028R,P063Y | 0.31 |
| R024W | D057G,P063Y | 0.31 |
| M032Q,L053K,N093R | T031R,P063Y,D105R | 0.31 |
| R024W,M032Q,L053K,N093R | D105R | 0.30 |
| 024W,M032Q,A049G,L053K,N093R | T031R,P063Y | 0.30 |
| N093R | D057G,P063Y | 0.30 |
| M032Q,A049G | S028R,D105R | 0.30 |
| R024W,L053K | D057G,P063Y | 0.29 |
| M032Q,A049G,N093R | S028R,T031R,D057G,P063Y,D105R | 0.29 |
| Humanized (SEQ ID No. 14) | D057G,P063Y | 0.29 |
| M032Q,A049G,N093R | S028R,P063Y | 0.29 |
| M032Q | T031R,D105R | 0.29 |
| R024W,M032Q | Humanized (SEQ ID No. 13) | 0.29 |
| M032Q,L053K,N093R | S028R,T031R,P063Y | 0.29 |
| M032Q,L053K | T031R,P063Y,D105R | 0.29 |
| R024W,L053K,N093R | D057G,P063Y | 0.28 |
| R024W,M032Q | D057G | 0.28 |
| A049G | S028R,P063Y | 0.28 |
| M032Q,L053K | S028R,T031R,P063Y | 0.28 |
| R024W,M032Q,A049G,N093R | S028R,T031R,P063Y | 0.27 |
| A049G | T031R,D057G | 0.27 |
| 024W,M032Q,A049G,L053K,N093R | P063Y,D105R | 0.27 |
| M032Q,A049G | S028R,D057G,P063Y,D105R | 0.26 |

FIGURE 6 (CONT'D)

| | | |
|---|---|---|
| M032Q,L053K | S028R,D057G,P063Y | 0.26 |
| R024W,M032Q,A049G,L053K,N093R | P063Y | 0.26 |
| M032Q,A049G | S028R,T031R,P063Y,D105R | 0.26 |
| M032Q | D057G,D105R | 0.26 |
| M032Q | D105R | 0.25 |
| R024W,M032Q | S028R,T031R,D057G | 0.25 |
| R024W,M032Q,N093R | P063Y,D105R | 0.25 |
| M032Q,L053K | S028R,P063Y | 0.24 |
| M032Q,N093R | S028R | 0.24 |
| R024W,M032Q | D057G,D105R | 0.24 |
| R024W,M032Q,L053K,N093R | S028R,T031R,D057G | 0.23 |
| R024W,L053K | S028R,D057G,P063Y,D105R | 0.23 |
| R024W,M032Q | S028R,T031R | 0.23 |
| R024W,M032Q,N093R | Humanized (SEQ ID No. 13) | 0.23 |
| Wild Type Chimera (SEQ ID No. 58) | Wild Type Chimera (SEQ ID No. 57) | 0.22 |

FIGURE 6 (CONT'D)

| Globo H (ng/mL) | Chimeric VK9 | Chimeric 2C2 | Humanized R28 |
|---|---|---|---|
| 1000 | 17448.0 | 509.0 | 71.4 |
| 500 | 2234.0 | 992.4 | 578.2 |
| 250 | 16663.0 | 1078.0 | 861.6 |
| Average | 12115.0 | 859.8 | 503.7 |
| Kd (M) | 1.21E-05 | 8.60E-07 | 5.04E-07 |

FIGURE 7

SEQUENCE LISTING

```
<160> NUMBER OF SEQ ID NOS: 60

<210> SEQ ID NO 1
<211> LENGTH: 12
<212> TYPE: PRT
<213> ORGANISM: Mus musculus

<400> SEQUENCE: 1

Gly Phe Ser Leu Tyr Thr Phe Asp Met Gly Val Gly
1               5                   10

<210> SEQ ID NO 2
<211> LENGTH: 16
<212> TYPE: PRT
<213> ORGANISM: Mus musculus

<400> SEQUENCE: 2

His Ile Trp Trp Asp Asp Asp Lys Tyr Tyr Asn Pro Ala Leu Lys Ser
1               5                   10                  15
```

<210> SEQ ID NO 3
<211> LENGTH: 13
<212> TYPE: PRT
<213> ORGANISM: Mus musculus

<400> SEQUENCE: 3

Val Arg Gly Leu His Asp Tyr Tyr Tyr Trp Phe Ala Tyr
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Synthetic: Humanized Heavy Chain Frame work 1

<400> SEQUENCE: 4

Gln Ile Thr Leu Lys Glu Ser Gly Pro Thr Leu Val Lys Pro Thr Gln
1               5                   10                  15

Thr Leu Thr Leu Thr Cys Thr Phe Ser
            20                  25

<210> SEQ ID NO 5
<211> LENGTH: 14
<212> TYPE: PRT
<213> ORGANISM: Artificial Sequence
<220> FEATURE:
<223> OTHER INFORMATION: Synthetic: Humanized Heavy Chain Frame work 2

<400> SEQUENCE: 5

Trp Ile Arg Gln Pro Pro Gly Lys Gly Leu Glu Trp Leu Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Synthetic: Humanized Heavy Chain Frame work 3

<400> SEQUENCE: 6

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 7
<211> LENGTH: 10
<212> TYPE: PRT
<213> ORGANISM: Mus musculus

<400> SEQUENCE: 7

Arg Ala Ser Ser Ser Val Ser Tyr Met His
1               5                   10

<210> SEQ ID NO 8
<211> LENGTH: 7
<212> TYPE: PRT
<213> ORGANISM: Mus musculus

<400> SEQUENCE: 8

Ala Thr Ser Asn Leu Ala Ser
1               5

```
<210> SEQ ID NO 9
<211> LENGTH: 9
<212> TYPE: PRT
<213> ORGANISM: Mus musculus

<400> SEQUENCE: 9

Gln Gln Trp Ser Arg Asn Pro Phe Thr
1               5

<210> SEQ ID NO 10
<211> LENGTH: 23
<212> TYPE: PRT
<213> ORGANISM: Artificial Sequence
<220> FEATURE:
<223> OTHER INFORMATION: Synthetic:   Humanized Light Chain Frame work 1

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic:   Humanized Light Chain Frame work 2

<400> SEQUENCE: 11

Trp Tyr Gln Gln Lys Pro Gly Lys Ser Pro Lys Pro Trp Ile Tyr
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: Synthetic:   Humanized Light Chain Frame work 3

<400> SEQUENCE: 12

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 13
<211> LENGTH: 112
<212> TYPE: PRT
<213> ORGANISM: Artificial Sequence
<220> FEATURE:
<223> OTHER INFORMATION: Synthetic:   Full-length Humanized Heavy Chain

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80
```

Val Leu Thr Met Thr Asn Met Asp Pro Val Asp Thr Ala Thr Tyr Tyr
            85                  90                  95

Cys Ala Arg Val Arg Gly Leu His Asp Tyr Tyr Tyr Trp Phe Ala Tyr
        100                 105                 110

<210> SEQ ID NO 14
<211> LENGTH: 96
<212> TYPE: PRT
<213> ORGANISM: Artificial Sequence
<220> FEATURE:
<223> OTHER INFORMATION: Synthetic:   Full-length Humanized Light Chain

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 15
<211> LENGTH: 112
<212> TYPE: PRT
<213> ORGANISM: Artificial Sequence
<220> FEATURE:
<223> OTHER INFORMATION: Synthetic:   S028K

<400> SEQUENCE: 15

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Lys Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Synthetic:   S028R

<400> SEQUENCE: 16

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Arg Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
                100                 105                 110

<210> SEQ ID NO 17
<211> LENGTH: 112
<212> TYPE: PRT
<213> ORGANISM: Artificial Sequence
<220> FEATURE:
<223> OTHER INFORMATION: Synthetic: S028Y

<400> SEQUENCE: 17

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Tyr Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
                100                 105                 110

<210> SEQ ID NO 18
<211> LENGTH: 112
<212> TYPE: PRT
<213> ORGANISM: Artificial Sequence
<220> FEATURE:
<223> OTHER INFORMATION: Synthetic: S028F

<400> SEQUENCE: 18

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Phe Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
                100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Synthetic: T031K

<400> SEQUENCE: 19

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Lys Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Synthetic: T031R

<400> SEQUENCE: 20

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Arg Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Synthetic: D057H

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
            35                  40                  45

Trp Leu Ala His Ile Trp Trp Asp His Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
               100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Synthetic:   D057G

<400> SEQUENCE: 22

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Gly Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
               100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Synthetic:   D057S

<400> SEQUENCE: 23

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Ser Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
               100                 105                 110

<210> SEQ ID NO 24

<211> LENGTH: 112
<212> TYPE: PRT
<213> ORGANISM: Artificial Sequence
<220> FEATURE:
<223> OTHER INFORMATION: Synthetic:  D057Q

<400> SEQUENCE: 24

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Tyr Thr Phe
            20                  25                  30
Asp Met Gly Val Gly Trp Ile Arg Gln Pro Pro Gly Lys Gly Leu Glu
        35                  40                  45
Trp Leu Ala His Ile Trp Trp Asp Gln Asp Lys Tyr Tyr Asn Pro Ala
    50                  55                  60
Leu Lys Ser Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Val Arg Gly Leu His Asp Tyr Tyr Tyr Trp Phe Ala Tyr
            100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: Synthetic:  D057W

<400> SEQUENCE: 25

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Tyr Thr Phe
            20                  25                  30
Asp Met Gly Val Gly Trp Ile Arg Gln Pro Pro Gly Lys Gly Leu Glu
        35                  40                  45
Trp Leu Ala His Ile Trp Trp Asp Trp Asp Lys Tyr Tyr Asn Pro Ala
    50                  55                  60
Leu Lys Ser Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Val Arg Gly Leu His Asp Tyr Tyr Tyr Trp Phe Ala Tyr
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: Synthetic:  P063H

<400> SEQUENCE: 26

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Tyr Thr Phe
            20                  25                  30
Asp Met Gly Val Gly Trp Ile Arg Gln Pro Pro Gly Lys Gly Leu Glu
        35                  40                  45
```

```
Trp Leu Ala His Ile Trp Trp Asp Asp Asp Lys Tyr Tyr Asn His Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110
```

<210> SEQ ID NO 27
<211> LENGTH: 112
<212> TYPE: PRT
<213> ORGANISM: Artificial Sequence
<220> FEATURE:
<223> OTHER INFORMATION: Synthetic: P063R

<400> SEQUENCE: 27

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Asp Lys Tyr Tyr Asn Arg Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: Synthetic: P063Y

<400> SEQUENCE: 28

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Asp Lys Tyr Tyr Asn Tyr Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: Synthetic: P063A

<400> SEQUENCE: 29

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Lys Tyr Tyr Asn Ala Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Synthetic: P063L

<400> SEQUENCE: 30

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Lys Tyr Tyr Asn Leu Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Synthetic: P063V

<400> SEQUENCE: 31

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Lys Tyr Tyr Asn Val Ala
    50                  55                  60

-continued

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Asp Tyr Tyr Tyr Trp Phe Ala Tyr
        100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Synthetic: D105R

<400> SEQUENCE: 32

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Arg Tyr Tyr Tyr Trp Phe Ala Tyr
        100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Synthetic: D105K

<400> SEQUENCE: 33

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Lys Tyr Tyr Tyr Trp Phe Ala Tyr
        100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Synthetic: D105G

<400> SEQUENCE: 34

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Gly Tyr Tyr Tyr Trp Phe Ala Tyr
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: Synthetic:   D105T

<400> SEQUENCE: 35

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Thr Tyr Tyr Tyr Trp Phe Ala Tyr
            100                 105                 110

<210> SEQ ID NO 36
<211> LENGTH: 112
<212> TYPE: PRT
<213> ORGANISM: Artificial Sequence
<220> FEATURE:
<223> OTHER INFORMATION: Synthetic:   D105M

<400> SEQUENCE: 36

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Ala Thr Tyr Tyr
            85                  90                  95

Cys Ala Arg Val Arg Gly Leu His Met Tyr Tyr Tyr Trp Phe Ala Tyr
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: Synthetic:   D105A

<400> SEQUENCE: 37

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Ala Tyr Tyr Tyr Trp Phe Ala Tyr
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: Synthetic:   D105I

<400> SEQUENCE: 38

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Val Arg Gly Leu His Ile Tyr Tyr Tyr Trp Phe Ala Tyr
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: Synthetic:   D105V

<400> SEQUENCE: 39

Gln Ile Thr Leu Lys Glu Ser Gly Pro Thr Leu Val Lys Pro Thr Gln

```
                1               5                   10                  15
            Thr Leu Thr Leu Thr Cys Thr Phe Ser Gly Phe Ser Leu Tyr Thr Phe
                            20                  25                  30

Asp Met Gly Val Gly Trp Ile Arg Gln Pro Pro Gly Lys Gly Leu Glu
                        35                  40                  45

Trp Leu Ala His Ile Trp Trp Asp Asp Asp Lys Tyr Tyr Asn Pro Ala
             50                  55                  60

Leu Lys Ser Arg Leu Thr Ile Ser Lys Asp Thr Ser Lys Asn Gln Val
             65                  70                  75                  80

Val Leu Thr Met Thr Asn Met Asp Pro Val Asp Thr Ala Thr Tyr Tyr
                            85                  90                  95

Cys Ala Arg Val Arg Gly Leu His Val Tyr Tyr Tyr Trp Phe Ala Tyr
                            100                 105                 110
```

<210> SEQ ID NO 40
<211> LENGTH: 96
<212> TYPE: PRT
<213> ORGANISM: Artificial Sequence
<220> FEATURE:
<223> OTHER INFORMATION: Synthetic:   R024G

<400> SEQUENCE: 40

```
            Glu Ile Val Leu Thr Gln Ser Pro Ala Thr Leu Ser Leu Ser Pro Gly
             1               5                   10                  15

Glu Arg Ala Thr Leu Ser Cys Gly Ala Ser Ser Ser Val Ser Tyr Met
                            20                  25                  30

His Trp Tyr Gln Gln Lys Pro Gly Lys Ser Pro Lys Pro Trp Ile Tyr
                        35                  40                  45

Ala Thr Ser Asn Leu Ala Ser Gly Val Pro Ser Arg Phe Ser Gly Ser
             50                  55                  60

Gly Ser Gly Thr Asp Phe Thr Phe Thr Ile Ser Ser Leu Gln Pro Glu
             65                  70                  75                  80

Asp Ile Ala Thr Tyr Tyr Cys Gln Gln Trp Ser Arg Asn Pro Phe Thr
                            85                  90                  95
```

<210> SEQ ID NO 41
<211> LENGTH: 96
<212> TYPE: PRT
<213> ORGANISM: Artificial Sequence
<220> FEATURE:
<223> OTHER INFORMATION: Synthetic:   R024S

<400> SEQUENCE: 41

```
            Glu Ile Val Leu Thr Gln Ser Pro Ala Thr Leu Ser Leu Ser Pro Gly
             1               5                   10                  15

Glu Arg Ala Thr Leu Ser Cys Ser Ala Ser Ser Ser Val Ser Tyr Met
                            20                  25                  30

His Trp Tyr Gln Gln Lys Pro Gly Lys Ser Pro Lys Pro Trp Ile Tyr
                        35                  40                  45

Ala Thr Ser Asn Leu Ala Ser Gly Val Pro Ser Arg Phe Ser Gly Ser
             50                  55                  60

Gly Ser Gly Thr Asp Phe Thr Phe Thr Ile Ser Ser Leu Gln Pro Glu
             65                  70                  75                  80

Asp Ile Ala Thr Tyr Tyr Cys Gln Gln Trp Ser Arg Asn Pro Phe Thr
                            85                  90                  95
```

<210> SEQ ID NO 42
<211> LENGTH: 96

```
<212> TYPE: PRT
<213> ORGANISM: Artificial Sequence
<220> FEATURE:
<223> OTHER INFORMATION: Synthetic:  R024W

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Trp Ala Ser Ser Val Ser Tyr Met
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 43
<211> LENGTH: 96
<212> TYPE: PRT
<213> ORGANISM: Artificial Sequence
<220> FEATURE:
<223> OTHER INFORMATION: Synthetic:  M032G

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Gly
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 44
<211> LENGTH: 96
<212> TYPE: PRT
<213> ORGANISM: Artificial Sequence
<220> FEATURE:
<223> OTHER INFORMATION: Synthetic:  M032Q

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Gln
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
```

<210> SEQ ID NO 45
<211> LENGTH: 96
<212> TYPE: PRT
<213> ORGANISM: Artificial Sequence
<220> FEATURE:
<223> OTHER INFORMATION: Synthetic: M032V

<400> SEQUENCE: 45

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Val
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95
```

<210> SEQ ID NO 46
<211> LENGTH: 96
<212> TYPE: PRT
<213> ORGANISM: Artificial Sequence
<220> FEATURE:
<223> OTHER INFORMATION: Synthetic: A049G

<400> SEQUENCE: 46

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Lys Ser Pro Lys Pro Trp Ile Tyr
        35                  40                  45

Gly Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95
```

<210> SEQ ID NO 47
<211> LENGTH: 96
<212> TYPE: PRT
<213> ORGANISM: Artificial Sequence
<220> FEATURE:
<223> OTHER INFORMATION: Synthetic: L053K

<400> SEQUENCE: 47

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Lys Ser Pro Lys Pro Trp Ile Tyr
        35                  40                  45

Ala Thr Ser Asn Lys Ala Ser Gly Val Pro Ser Arg Phe Ser Gly Ser
    50                  55                  60
```

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 48
<211> LENGTH: 96
<212> TYPE: PRT
<213> ORGANISM: Artificial Sequence
<220> FEATURE:
<223> OTHER INFORMATION: Synthetic: L053G

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Tyr Gln Gln Lys Pro Gly Lys Ser Pro Lys Pro Trp Ile Tyr
            35                  40                  45

Ala Thr Ser Asn Gly Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 49
<211> LENGTH: 96
<212> TYPE: PRT
<213> ORGANISM: Artificial Sequence
<220> FEATURE:
<223> OTHER INFORMATION: Synthetic: L053T

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Tyr Gln Gln Lys Pro Gly Lys Ser Pro Lys Pro Trp Ile Tyr
            35                  40                  45

Ala Thr Ser Asn Thr Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 50
<211> LENGTH: 96
<212> TYPE: PRT
<213> ORGANISM: Artificial Sequence
<220> FEATURE:
<223> OTHER INFORMATION: Synthetic: N093R

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Tyr Gln Gln Lys Pro Gly Lys Ser Pro Lys Pro Trp Ile Tyr
            35                  40                  45

Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Arg Arg Pro Phe Thr
                 85                  90                  95

<210> SEQ ID NO 51
<211> LENGTH: 96
<212> TYPE: PRT
<213> ORGANISM: Artificial Sequence
<220> FEATURE:
<223> OTHER INFORMATION: Synthetic:    N093Q

<400> SEQUENCE: 51

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
                 20                  25                  30

His Trp Tyr Gln Gln Lys Pro Gly Lys Ser Pro Lys Pro Trp Ile Tyr
            35                  40                  45

Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Arg Gln Pro Phe Thr
                 85                  90                  95

<210> SEQ ID NO 52
<211> LENGTH: 96
<212> TYPE: PRT
<213> ORGANISM: Artificial Sequence
<220> FEATURE:
<223> OTHER INFORMATION: Synthetic:    N093S

<400> SEQUENCE: 52

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
                 20                  25                  30

His Trp Tyr Gln Gln Lys Pro Gly Lys Ser Pro Lys Pro Trp Ile Tyr
            35                  40                  45

Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Arg Ser Pro Phe Thr
                 85                  90                  95

<210> SEQ ID NO 53
<211> LENGTH: 96
<212> TYPE: PRT
<213> ORGANISM: Artificial Sequence
<220> FEATURE:
<223> OTHER INFORMATION: Synthetic:    N093T

<400> SEQUENCE: 53

Glu Ile Val Leu Thr Gln Ser Pro Ala Thr Leu Ser Leu Ser Pro Gly

```
            1               5                  10                 15
Glu Arg Ala Thr Leu Ser Cys Arg Ala Ser Ser Ser Val Ser Tyr Met
            20                 25                 30

His Trp Tyr Gln Gln Lys Pro Gly Lys Ser Pro Lys Pro Trp Ile Tyr
            35                 40                 45

Ala Thr Ser Asn Leu Ala Ser Gly Val Pro Ser Arg Phe Ser Gly Ser
            50                 55                 60

Gly Ser Gly Thr Asp Phe Thr Phe Thr Ile Ser Ser Leu Gln Pro Glu
 65                 70                 75                 80

Asp Ile Ala Thr Tyr Tyr Cys Gln Gln Trp Ser Arg Thr Pro Phe Thr
                    85                 90                 95

<210> SEQ ID NO 54
<211> LENGTH: 96
<212> TYPE: PRT
<213> ORGANISM: Artificial Sequence
<220> FEATURE:
<223> OTHER INFORMATION: Synthetic:   N093F

<400> SEQUENCE: 54

Glu Ile Val Leu Thr Gln Ser Pro Ala Thr Leu Ser Leu Ser Pro Gly
 1               5                  10                 15

Glu Arg Ala Thr Leu Ser Cys Arg Ala Ser Ser Ser Val Ser Tyr Met
            20                 25                 30

His Trp Tyr Gln Gln Lys Pro Gly Lys Ser Pro Lys Pro Trp Ile Tyr
            35                 40                 45

Ala Thr Ser Asn Leu Ala Ser Gly Val Pro Ser Arg Phe Ser Gly Ser
            50                 55                 60

Gly Ser Gly Thr Asp Phe Thr Phe Thr Ile Ser Ser Leu Gln Pro Glu
 65                 70                 75                 80

Asp Ile Ala Thr Tyr Tyr Cys Gln Gln Trp Ser Arg Phe Pro Phe Thr
                    85                 90                 95

<210> SEQ ID NO 55
<211> LENGTH: 96
<212> TYPE: PRT
<213> ORGANISM: Artificial Sequence
<220> FEATURE:
<223> OTHER INFORMATION: Synthetic:   N093L

<400> SEQUENCE: 55

Glu Ile Val Leu Thr Gln Ser Pro Ala Thr Leu Ser Leu Ser Pro Gly
 1               5                  10                 15

Glu Arg Ala Thr Leu Ser Cys Arg Ala Ser Ser Ser Val Ser Tyr Met
            20                 25                 30

His Trp Tyr Gln Gln Lys Pro Gly Lys Ser Pro Lys Pro Trp Ile Tyr
            35                 40                 45

Ala Thr Ser Asn Leu Ala Ser Gly Val Pro Ser Arg Phe Ser Gly Ser
            50                 55                 60

Gly Ser Gly Thr Asp Phe Thr Phe Thr Ile Ser Ser Leu Gln Pro Glu
 65                 70                 75                 80

Asp Ile Ala Thr Tyr Tyr Cys Gln Gln Trp Ser Arg Leu Pro Phe Thr
                    85                 90                 95

<210> SEQ ID NO 56
<211> LENGTH: 96
<212> TYPE: PRT
<213> ORGANISM: Artificial Sequence
<220> FEATURE:
```

<223> OTHER INFORMATION: Synthetic:   N093M

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Leu Gln Pro Glu
65                  70                  75                  80

Asp Ile Ala Thr Tyr Tyr Cys Gln Gln Trp Ser Arg Met Pro Phe Thr
                85                  90                  95

<210> SEQ ID NO 57
<211> LENGTH: 112
<212> TYPE: PRT
<213> ORGANISM: Artificial Sequence
<220> FEATURE:
<223> OTHER INFORMATION: Synthetic:   Heavy Chain Variable Region of
      Chimeric Antibody

<400> SEQUENCE: 57

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Tyr Thr Phe
            20                  25                  30

Asp Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Val Ser Lys Asp Thr Ser Lys Asn Gln Val
65                  70                  75                  80

Phe Leu Lys Ile Pro Asn Val Asp Thr Ala Asp Ser Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 58
<211> LENGTH: 96
<212> TYPE: PRT
<213> ORGANISM: Artificial Sequence
<220> FEATURE:
<223> OTHER INFORMATION: Synthetic:   Light Chain Variable Region of
      Chimeric Antibody

<400> SEQUENCE: 58

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys Gln Gln Trp Ser Arg Asn Pro Phe Thr
                    85                  90                  95

<210> SEQ ID NO 59
<211> LENGTH: 453
<212> TYPE: PRT
<213> ORGANISM: Artificial Sequence
<220> FEATURE:
<223> OTHER INFORMATION: Synthetic: Heavy Chain Variable Region of
      Chimeric Antibody R28

<400> SEQUENCE: 59

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
                20                  25                  30

Asp Met Gly Val Gly Trp Ile Arg Gln Pro Pro Gly Lys Gly Leu Glu
            35                  40                  45

Trp Leu Ala His Ile Trp Trp Asp Gly Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Arg Tyr Tyr Tyr Trp Phe Ala Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro

```
                    340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
                435                 440                 445
Leu Ser Pro Gly Lys
            450

<210> SEQ ID NO 60
<211> LENGTH: 213
<212> TYPE: PRT
<213> ORGANISM: Artificial Sequence
<220> FEATURE:
<223> OTHER INFORMATION: Synthetic:   Light Chain Variable Region of
      Chimeric Antibody R28 (HC08)

<400> SEQUENCE: 60

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Ser Ser Val Ser Tyr Met
            20                  25                  30
His Trp Tyr Gln Gln Lys Pro Gly Lys Ser Pro Lys Pro Trp Ile Tyr
        35                  40                  45
Ala Thr Ser Asn Lys Ala Ser Gly Val Pro Ser Arg Phe Ser Gly Ser
    50                  55                  60
Gly Ser Gly Thr Asp Phe Thr Phe Thr Ile Ser Ser Leu Gln Pro Glu
65                  70                  75                  80
Asp Ile Ala Thr Tyr Tyr Cys Gln Gln Trp Ser Arg Arg Pro Phe Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

CARBOHYDRATE ANTIBODIES, PHARMACEUTICAL COMPOSITIONS AND USES THEREOF

REFERENCE TO SEQUENCE LISTING SUBMITTED VIA EFS-WEB

This application includes an electronically submitted sequence listing in .txt format. The .txt file contains a sequence listing entitled 2011-006 DIV ST25.txt created on Oct. 11, 2019 and is 56,031 bytes in size. The sequence listing contained in this .txt file is part of the specification and is hereby incorporated by reference herein in its entirety.

This application is a divisional of U.S. patent application Ser. No. 15/288,562, filed Oct. 7, 2016, which claims the benefit of priority from U.S. Provisional Patent Application No. 62/238,680, filed Oct. 7, 2015, the entire content of which is incorporated herein by reference.

FIELD

The present invention relates to modified antibodies to tumor-associated carbohydrate antigens, having some specific amino acid substitutions relative to the unmodified antibodies, as well as the unmodified antibodies. The present invention also relates to the use of these antibodies in the treatment, prevention or management of diseases or disorders, such as cancer or the inhibition of cancer cells.

BACKGROUND

Numerous surface carbohydrates are expressed in malignant tumor cells. For example, Globo H (Fuc α1→2Galβ1→3GalNAcβ1→3Gal a1→4Galβ1→4Glc) has been shown to be overexpressed on a variety of epithelial cancers and is associated with tumor aggressiveness and poor prognosis in breast cancer and small cell lung carcinoma.

These findings support therapeutic rationales designed to counteract the activities of the tumor-associated carbohydrates. In particular, antibodies that bind to the tumor-associate carbohydrates are drawing more attentions as a means to treat or inhibit cancer cells, as they have longer half-life in plasma and fewer adverse effects. Some earliest antibodies were mouse monoclonal antibodies (mAbs), secreted by hybridomas prepared from lymphocytes of mice immunized with these tumor associated carbohydrates. However, there are problems associated with the use of mouse antibodies in human, such as inability to trigger certain human effector function and adverse reaction including cytokine releases syndrome. Antibodies derived from a nonhuman animal species are humanized to enhance the effector function utility and/or lower the adverse reaction. However, a humanized antibody does not have a comparable binding activity as the non-humanized antibody.

There is still an unmet need to optimize the binding affinity of a humanized antibody. The present invention provides antibodies with optimized binding affinity to satisfy these and other needs.

SUMMARY OF THE INVENTION

The present invention provides for antibodies, or antigen-binding portions thereof, comprising a variable region that bind to a carbohydrate antigen or a fragment thereof.

In one embodiment, the present invention provides for an antibody, or an antigen-binding portion thereof, that binds to a carbohydrate antigen or a fragment thereof and comprises a heavy chain variable region, wherein the heavy chain variable region comprises three complementarity determining regions (CDRs), CDR1, CDR2 and CDR3, having amino acid sequences about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively, wherein the CDR comprises at least one amino acid substitution selected from: (a) Amino acid residue 28 in CDR1 is substituted with a basic amino acid, a neutral amino acid with the proviso that the neutral amino acid is not Serine, or a hydrophobic amino acid; (b) Amino acid residue 31 in CDR1 is substituted with a basic amino acid; (c) Amino acid residue 57 in CDR2 is substituted with a neutral, a basic or a hydrophobic amino acid; (d) Amino acid residue 63 in CDR2 is substituted with a neutral amino acid, a basic amino acid or a hydrophobic amino acid with the proviso that the hydrophobic amino acid is not Proline, or (e) Amino acid residue 105 in CDR3 is substituted with a basic amino acid, a hydrophobic amino acid or a neutral amino acid.

In another embodiment, the present invention provides for an antibody, or an antigen-binding portion thereof, that binds to a carbohydrate antigen or a fragment thereof and comprises a light chain variable region, wherein the light chain variable region comprises three CDRs, CDR1, CDR2 and CDR3, having amino acid sequences about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively; wherein the CDR comprises at least one amino acid substitution selected from (a) amino acid residue 24 in CDR1 is substituted with a neutral or a hydrophobic amino acid, (b) amino acid residue 32 in CDR1 is substituted with a neutral amino acid or a hydrophobic amino acid other than Methionine, (c) amino acid residue 49 in CDR2 is substituted with a neutral amino acid, (d) amino acid residue 53 in CDR2 is substituted with a neutral or a basic amino acid, or (e) amino acid residue 93 in CDR3 is substituted with a basic amino acid, a hydrophobic amino acid or a neutral amino acid other than Asparagine.

In yet another embodiment, the present invention provides for an antibody, or an antigen-binding portion thereof, comprises (i) a heavy chain variable region, wherein the heavy chain variable region comprises three CDRs, CDR1, CDR2 and CDR3, having amino acid sequences about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively, wherein the heavy chain comprises at least one amino acid substitution selected from: (a) Amino acid residue 28 in CDR1 is substituted with a basic amino acid, a neutral amino acid with the proviso that the neutral amino acid is not Serine, or a hydrophobic amino acid; (b) Amino acid residue 31 in CDR1 is substituted with a basic amino acid; (c) Amino acid residue 57 in CDR2 is substituted with a neutral, a basic or a hydrophobic amino acid; (d) Amino acid residue 63 in CDR2 is substituted with a neutral amino acid, a basic amino acid or a hydrophobic amino acid, with the proviso that the hydrophobic amino acid is not Proline, or (e) Amino acid residue 105 in CDR3 is substituted with a basic amino acid, a hydrophobic amino acid or a neutral amino acid, and (ii) a light chain variable region, wherein the light chain variable region comprises three CDRs, CDR1, CDR2 and CDR3, having amino acid sequences about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively; wherein the light chain comprises at least one amino acid substitution selected from (a) amino acid residue 24 in CDR1 is substituted with a neutral or a hydrophobic amino acid, (b) amino acid residue 32 in CDR1 is substituted with a neutral amino acid or a hydrophobic amino acid other than Methionine, (c) amino acid residue 49 in CDR2 is substituted with a neutral amino acid, (d) amino acid residue 53 in CDR2 is substituted with a neutral amino acid or a basic amino acid, or (e) amino acid residue 93 in CDR3 is substituted with a basic amino acid, a hydrophobic amino acid or neutral amino acid other than Asparagine.

In a fourth embodiment, the present invention provides an antibodies or an antigen-binding portion thereof, comprises (a) a heavy chain variable region, wherein the heavy chain variable region comprise three CDRs, CDR1, CDR2 and CDR3, having amino acid sequences about 90%, about 91%, about 92%, about 93%, about 94%, about 95%, about 96%, about 97%, about 98%, about 99% or about 100% homologous to the amino acid sequences set forth in SEQ ID NOs: 1, 2 and 3, respectively, and/or (b) a light chain variable region, wherein the light chain variable region comprises three CDRs, CDR1, CDR2 and CDR3, having amino acid sequences about 90%, about 91%, about 92%, about 93%, about 94%, about 95%, about 96%, about 97%, about 98%, about 99% or about 100% homologous to the amino acid sequences set forth in SEQ ID NOs: 7, 8 and 9, respectively.

Some embodiments provide pharmaceutical compositions comprising the antibody or antigen-binding portion thereof as described herein and at least one pharmaceutically acceptable earner.

Some embodiments also provide for methods of inhibiting cancer cells, comprising administering to a subject in need thereof an effective amount of the antibody or antigen-binding portion thereof described herein. In one embodiment, the cancer cells are Globo H expressing cancer cells.

BRIEF DESCRIPTION OF THE DRAWINGS

FIG. 1A illustrates the amino acid sequence of an exemplary embodiment of the heavy chain variable region of the unmodified humanized antibody (SEQ ID NO. 13). FIG. 1B illustrates the amino acid sequence of an exemplary embodiment of the light chain variable region of the unmodified humanized antibody (SEQ ID NO. 14).

FIGS. 4A-4E illustrate the optical density ($OD_{450}$ nm) of modified antibodies with one amino acid (AA) substitution at residue 28 (FIG. 4A), residue 31 (FIG. 4B), residue 57 (FIG. 4C), residue 63 (FIG. 4D) and residue 105 (FIG. 4E) of the heavy chain variable region of the humanized antibody and that of the wild type (WT) chimeric antibody.

FIGS. 5A-5E illustrate $OD_{450}$ nm of modified antibodies with one amino acid substitution at residue 24 (FIG. 5A), residue 32 (FIG. 5B), residue 49 (FIG. 5C), residue 53 (FIG. 5D) and residue 93 (FIG. 5E) of the light chain variable region of the humanized antibody and that of the wild type chimeric antibody.

FIG. 6 illustrates $OD_{450}$ nm of modified antibodies with at least two amino acid substitutions (Combinatorial Protein Synthesis mutants) which are higher than that of the wild type chimeric antibody.

FIG. 7 illustrates the comparison of dissociation constant (Kd) of chimeric antibody derived from hybridoma VK9 (originated from Memorial Sloan Kettering Cancer Center, MSKCC), chimeric antibody derived from hybridoma 2C2 (SEQ ID NOs: 57 and 58) and one exemplary embodiment of the modified antibody (humanized R28 mAbs, SEQ ID NOs: 59 and 60) with different concentrations of Globo H.

DETAILED DESCRIPTION OF THE INVENTION

Figures 2, 3:
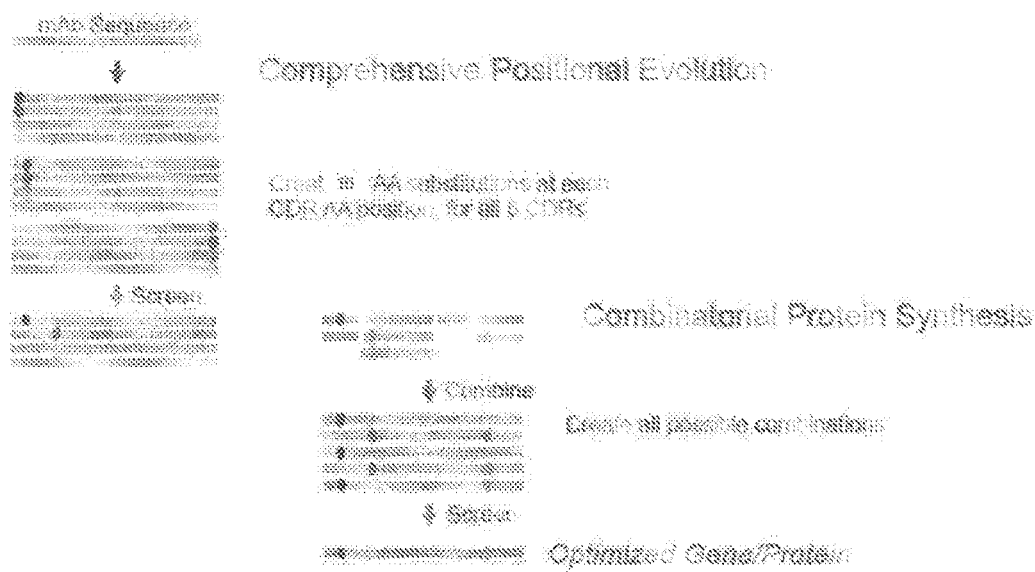
FIG. 2 illustrates the optical density ($OD_{450}$nm) of one exemplary embodiment of the chimeric antibody (Heavy chain: SEQ ID NO. 57 and Light chain: SEQ ID NO. 58) and one exemplary embodiment of the humanized antibody (Heavy chain: SEQ ID NO. 13 and Light chain: SEQ ID NO. 14).
FIG. 3 illustrates schematically the process for Comprehensive Positional Evolution and Combinatorial Protein Synthesis.

As used herein, the articles "a" and "an" refer to one or more than one (i.e., at least one) of the grammatical object of the article. By way of example, "an element" means one element or more than one element.

An "effective amount," as used herein, refers to a dose of the antibody or pharmaceutical composition that is sufficient to reduce the symptoms and signs of cancer, such as weight loss, pain and palpable mass, which is detectable, either clinically as a palpable mass or radiologically through various imaging means. The term "effective amount" and "therapeutically effective amount" are used interchangeably.

The term "subject" can refer to a vertebrate having cancer or to a vertebrate deemed to be in need of cancer treatment. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "antibody" is intended to encompass antibodies, digestion fragments, specified portions and variants thereof, including antibody mimetics or comprising portions of antibodies that mimic the structure and/or function of an antibody or a specified fragment or portion thereof, including single chain antibodies and fragments thereof, each containing at least one CDR derived from an antibody of the present invention. Antibodies include antibody fragments, antibody variants, monoclonal antibodies, polyclonal antibodies, and recombinant antibodies and the like. Antibodies can be generated in mice, rabbits or humans.

The antibodies can be full-length or can comprise a fragment (or fragments) of the antibody having an antigen-binding portion, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), FIT or scFv (e.g., by molecular biology techniques), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, bispecific and multispecific antibodies formed from antibody fragments.

Single chain antibodies produced by joining antibody fragments using recombinant methods, or a synthetic linker, are also encompassed by the present invention. Bird et al., Science, 1988, 242:423-426. Huston et al., Proc. Natl. Acad. Sci. USA, 1988, 85:5879-5883.

Multispecific or bi-specific antibodies or fragments thereof may be specific for different epitopes of one target carbohydrate (e.g., Globo H) or may contain antigen-binding domains specific for more than one target carbohydrate (e.g., antigen-binding domains specific for Globo H, SSEA-3 and SSEA-4). In one embodiment, a multispecific antibody or antigen-binding portion thereof comprises at least two different variable domains, wherein each variable domain is capable of specifically binding to a separate carbohydrate antigen or to a different epitope on the same carbohydrate antigen. Tutt et al., 1991, J. Immunol. 147:60-69. Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The antibodies or antigen-binding portions may be peptides. Such peptides can include variants, analogs, orthologs, homologs and derivatives of peptides, that exhibit a biological activity, e.g., binding to a tumor-associate carbohydrate antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A One type of derivatized protein is produced by crosslinking two or more proteins (of the same type or of different types). Suitable cross linkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

An antibody light or heavy chain variable region comprises a framework region (FW) interrupted by three hypervariable regions, referred to as complementarity determining regions or CDRs. According to one aspect of the invention, the antibody or the antigen-binding portion thereof may have the following structure:

Leader Sequence-FW1-CDR1-FW2-CDR2-FW3-CDR3- wherein the ammo acid sequences of FW1, FW2, FW3, CDR1, CDR2 and CDR3 of the present invention are disclosed in Table 1.

The heavy chain and light chain variable regions of the present antibodies or antigen-binding portions thereof can be from a non-human or human source. The framework of the present antibodies or antigen-binding portions thereof can be human, humanized, non-human (e.g., a murine framework modified to decrease antigenicity in humans), or a synthetic framework (e.g., a consensus sequence).

Antibodies of the present invention also include chimerized or humanized monoclonal antibodies, generated from non-human (e.g., murine) antibodies of a hybridoma clone. Also encompassed by the present invention are antibodies or antigen-binding portions thereof comprising one or two variable regions as disclosed herein, wherein certain sequences of the variable region, such as the framework sequence, replaced by sequences from at least one different species including, but not limited to, human, rabbits, sheep, dogs, cats, cows, horses, goats, pigs, monkeys, apes, gorillas, chimpanzees, ducks, geese, chickens, amphibians, reptiles and other animals.

The term "humanized antibody" refers to an antibody comprising at least one human framework and at least one, preferably all CDRs from a non-human antibody, and in which any constant region present is substantially homologous to a human antibody constant region, i.e., about 85-90%, at least about 90%, at least about 95% homologous. Hence, all parts of a humanized antibody, except possibly the CDR, are substantially homologous to corresponding parts of one or more human antibody sequences. Humanized antibodies can be generated by replacing sequences of the variable region that are not directly involved in antigen-binding (e.g., framework) with equivalent sequences from human variable regions. Techniques for obtaining humanized antibodies are routinely available to the skilled person, they have been described, inter alia, in U.S. Pat. Nos. 5,225,539; 6,548,640; and 6,982,321. Those techniques are well known in the art, include isolating, manipulating, and expressing the nucleic acid sequences that encode all or part of variable regions from at least one of a heavy or light chain. For example, once non-human (e.g., murine) antibodies are obtained, variable regions can be sequenced, and the location of the CDRs and frameworks residues determined. Kabat, E. A, et al. (1991) Sequences of Proteins of Immunological Interest, Fifth Edition, U.S. Department of Health and Human Services, NIH Publication NO. 91-3242. Chothia, C. et al. (1987) J. Mol. Biol., 196:901-917. DNA encoding the light and heavy chain variable regions can, optionally, be ligated to corresponding constant regions and then subcloned into an appropriate expression vector. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in Table 1) or only some of the CDRs may be replaced. It is only necessary to keep the CDRs required for binding of the antibody to a predetermined carbohydrate antigen (e.g., Globo H). Morrison, S. L., 1985, Science, 229:1202-1207. Oi et al., 1986, BioTechniques, 4:214. U.S. Pat. Nos.: 5,585,089; 5,225,539; 5,693,761 and 5,693,762. EP 519596. Jones et al., 1986, Nature, 321:552-525. Verhoeyan et al., 1988, Science, 239:1534. Beidler et al., 1988, J. Immunol., 141:4053- 4060.

A chimeric antibody is a molecule in which different portions are derived from different animal species. For example, a chimeric antibody may contain a variable region derived from a murine mAb and a human immunoglobulin constant region. Human constant region DNA sequences can be isolated in accordance with well-known procedures from a variety of human cells (see Kabat et al., 1991; and WO 87/02671). Chimeric antibodies can be produced by recombinant DNA techniques. Morrison, etal., Proc Natl Acad Sci, 81:6851-6855 (1984). For example, a gene encoding a murine (or other species) antibody molecule is digested with restriction enzymes to remove the region encoding the murine Fc, and the equivalent portion of a gene encoding a human Fc constant region is then substituted into the recombinant DNA molecule. Chimeric antibodies can also be created by recombinant DNA techniques where DNA encoding murine V regions can be ligated to DNA encoding the human constant regions. Better et al., Science, 1988, 240: 1041-1043. Liu et al. PNAS, 1987 84:3439-3443. Liu et al., J. Immunol., 1987, 139:3521-3526. Sun et al. PNAS, 1987, 84:214-218. Nishimura et al., Canc. Res., 1987, 47:999-1005. Wood et al. Nature, 1985, 314:446-449. Shaw et al., Natl. Cancer Inst., 1988, 80:1553-1559. International Patent Publication NOs: WO1987002671 and WO 86/01533. European Patent Application NOs: 184, 187; 171,496; 125,023; and 173,494. U.S. Pat. No. 4,816,567.

All antibody isotypes are encompassed by the present invention, including IgG (e.g., IgG1, IgG2, IgG3, IgG4), IgM, IgA (IgA1, IgA2), IgD or IgE (all classes and sub-classes are encompassed by the present invention). The antibodies or antigen-binding portions thereof may be mammalian (e.g., mouse, human) antibodies or antigen-binding portions thereof. The light chains of the antibody may be of kappa or lambda type.

The terms "wild type antibody" and "unmodified antibody" are used interchangeably and as used herein refer to an antibody comprising an amino acid sequence which lacks one or more of amino acid substitutions disclosed herein.

The term "substitution" can refer to the replacement of an amino acid at a particular position in an unmodified or wild type amino acid sequence with another amino acid. For example, the substitution S28K refers to Serine at position 28, by Kabat numbering system, is replaced with Lysine.

Also within the scope of the invention are antibodies or antigen-binding portions thereof in which specific amino acids have been substituted, deleted or added. In an exemplary embodiment, these alternations (i.e., conservative substitution, conservative deletion or conservative addition) do not have a substantial effect on the peptide's biological properties such as the effector function or the binding affinity. For purposes of classifying amino acids alteration as conservative or non-conservative, amino acids may be grouped as follows: hydrophobic, neutral, acidic, and basic (see Table 2 for more details). Conservative substitutions involve substitutions between amino acids in the same group. Non-conservative substitutions constitute exchanging a member of one of these groups for a member of another. Ng et al. (Predicting the Effects of Amino Acid Substitutions on Protein Function, Annu. Rev. Genomics Hum. Genet. 2006. 7:61-80) provides an overview of various amino acid substitution (AAS) prediction methods to allow a skilled artisan to predict and select an amino acid substitution, without changing the protein function.

In another exemplary embodiment, antibodies may have amino acid substitutions in the CDRs, such as to improve binding affinity of the antibody to the antigen. In yet another exemplary embodiment, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

According to one aspect of the invention, the amino acid substitutions described herein occur at positions corresponding to the Kabat numbering scheme (e.g., Kabat et al., Sequences of Immunological Interest. 5th Ed. Public Health Service, National Institutes of Health, Bethesda, Md. (1991)).

Antibodies, or antigen-binding fragments, variants or derivatives thereof of the present disclosure can also be described or specified in terms of their binding affinity to an antigen. "Affinity" refers to the strength of the sum total of noncovalent interactions between a single binding site of a molecule (e.g., an antibody) and its binding partner (e.g., a tumor associated carbohydrate). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. The affinity of an antibody for a carbohydrate antigen can be determined experimentally using any suitable method, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); or ELISA method.

The present antibodies or antigen-binding portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region. DNA can be expressed in various suitable cells, including prokaryotic and eukaryotic cells, e.g., bacterial cells, (e.g., E. coli), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, unmodified cells, derivatives and/or engineered variants of monkey kidney cells (COS, e.g., COS-1, COS-7), HEK293, baby hamster kidney (BHK, e.g., BHK21), Chinese hamster ovary (CHO), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

All numbers herein are approximations and may be modified by "about."

Unmodified Antibodies

The present invention provides antibodies or the antigen-binding portions thereof, without at least one amino acid substitution disclosed herein (unmodified or wild type antibody).

In one aspect of the invention, the unmodified antibody or the antigen-binding portion thereof comprises a heavy chain variable region, wherein the heavy chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively.

In some embodiments, the heavy chain variable region of the unmodified antibody or the antigen-binding portion thereof further comprises at least one framework selected from (i) a framework between a leader sequence and said CDR1 of the heavy chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 4, (ii) a framework between said CDR1 and said CDR2 of the heavy chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 5, or (iii) a framework between said CDR2 and said CDR3 of the heavy chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 6.

In other embodiment, amino acid residue 46 in framework 2 (or the 6th amino acid residue from the C-terminal of framework 2) of the heavy chain variable region (SEQ ID NO.5) is glycine and not substituted. The position of the amino acid residues of SEQ ID NO. 5 is illustrated below:

| Amino Acid Residue | | | | | | | | | | | | | | |
|---|---|---|---|---|---|---|---|---|---|---|---|---|---|---|
| | W* | I | R | Q | P | P | G | K | G | L | E | W | L | A** |
| Position NO. | 38 | 39 | 40 | 41 | 42 | 43 | 44 | 45 | 46 | 47 | 48 | 49 | 50 | 51 |

*Amino acid residue 38 of framework 2 (W) is the residue adjacent to CDR 1 or the first amino acid residue from the N terminal of framework 2.
**Amino acid residue 51 of framework 2 (A) is the residue adjacent to CDR2 or the first amino acid residue from the C-terminal of framework 2.

In another aspect of the invention, the unmodified antibody or the antigen-binding portion thereof comprises a light chain variable region, wherein the light chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively.

In some embodiments, the light chain variable region of the unmodified antibody or the antigen-binding portion thereof further comprises at least one framework selected from (a) a framework between a leader sequence and said CDR1 of the light chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 10, (b) a framework between said CDR1 and said CDR2 of the light heavy chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 11, or (c) a framework between said CDR2 and said CDR3 of the light chain, having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 12.

In other embodiment, amino acid residue 45 in framework 2 (or the 4th amino acid residue from the C-terminal of framework 2) of the light chain (SEQ ID NO. 11) is proline and/or amino acid residue 46 in framework 2 (the 3rd amino acid residue from the C-terminal of framework 2) of the light chain is tryptophan, with the proviso that amino acid residue 45 and/or amino acid residue 46 not substituted. The position of the amino acid of SEQ ID NO: 11 is illustrated below:

| Amino Acid Residue | | | | | | | | | | | | | | |
|---|---|---|---|---|---|---|---|---|---|---|---|---|---|---|
| | W* | Y | Q | Q | K | P | G | K | S | P | K | P | W | I | Y** |
| Position NO. | 34 | 35 | 36 | 37 | 38 | 39 | 40 | 41 | 42 | 43 | 44 | 45 | 46 | 47 | 48 |

*The amino acid at position 34 of framework 2 (W) is the residue adjacent to CDR 1 or the first amino acid residue from the N-terminal of framework 2.
**The amino acid at position 48 of framework 2 (Y) is the residue adjacent to CDR2 or the first amino acid residue from the C-terminal of framework 2.

The unmodified antibodies of the present invention also include humanized antibodies that bind to a tumor carbohydrate or a fragment thereof. In one embodiment, the humanized antibody comprises a heavy chain variable region having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 13, and/or a light chain variable region comprises a light chain having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 14.

The unmodified antibodies of the present invention also include chimeric antibodies that bind to a tumor carbohydrate or a fragment thereof. In one embodiment, the chimeric antibody comprises a heavy chain variable region having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 57, and/or a light chain variable region comprises a light chain having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 58.

In some embodiments, the unmodified antibodies or the antigen-binding portions thereof are produced from non-human antibodies obtained from the hybridoma designated 2C2 (deposited under ATCC Accession No.: PTA-121138). See PCT/US15/25305, the content of which is incorporated by reference in its entirety.

Table 1 shows the amino acid sequences of the heavy chain variable region, the light chain variable region, the CDRs, and FWs of the unmodified antibodies and one exemplary embodiment of the modified antibodies.

TABLE 1

| Variable Region | Amino Acid Sequences | SEQ ID NO |
| --- | --- | --- |
| Heavy Chain CDR1 | GFSLYTFDMGVG | 1 |
| Heavy Chain CDR2 | HIWWDDDKYYNPALKS | 2 |
| Heavy Chain CDR3 | VRGLHDYYYWFAY | 3 |
| Humanized Heavy Chain FW1 | QITLKESGPTLVKPTQTLTL TCTFS | 4 |
| Humanized Heavy Chain FW2 | WIRQPPGKGLEWLA | 5 |
| Humanized Heavy Chain FW3 | RLTISKDTSKNQVVLTMTNM DPVDTATYYCAR | 6 |
| Light Chain CDR1 | RASSSVSYMH | 7 |
| Light Chain CDR2 | ATSNLAS | 8 |
| Light Chain CDR3 | QQWSRNPFT | 9 |
| Humanized Light Chain FW1 | EIVLTQSPATLSLSPGERAT LSC | 10 |
| Humanized Light Chain FW2 | WYQQKPGKSPKPWIY | 11 |
| Humanized Light Chain FW3 | GVPSRFSGSGSGTDFTFTIS SLQPEDIATYYC | 12 |
| Heavy Chain Variable Region Of Humanized Antibody | QITLKESGPTLVKPTQTLTL TCTFSGFSLYTFDMGVGWIR QPPGKGLEWLAHIWWDDDKY YNPALKSRLTISKDTSKNQV VLTMTNMDPVDTATYYCARV RGLHDYYYWFAY | 13 |
| Light Chain Variable Region Of Humanized Antibody | EIVLTQSPATLSLSPGERAT LSCRASSSVSYMHWYQQKPG KSPKPWIYATSNLASGVPSR FSGSGSGTDFTFTISSLQPE DIATYYCQQWSRNPFT | 14 |
| Heavy Chain Variable Region Of Chimeric Antibody | QVTLKESGPGILQPSQTLSL TCSFSGFSLYTFDMGVGWIR QPSGKGLEWLAHIWWDDDKY YNPALKSRLTVSKDTSKNQV FLKIPNVDTADSATYYCARV RGLHDYYYWFAY | 57 |
| Light Chain Variable Region Of Chimeric Antibody | QIVLSQSPTILSASPGEKVT MTCRASSSVSYMHWYQQKPG SSPKPWIYATSNLASGVPAR FSGSGSGTSYSLTISRVEAE DAATYFCQQWSRNPFT | 58 |
| Heavy Chain Variable Region Of Modified Antibody (Humanized R28 mAb) | QITLKESGPTLVKPTQTLTL TCTFSGFSLYTFDMGVGWIR QPPGKGLEWLAHIWWDGDKY YNPALKSRLTISKDTSKNQV VLTMTNMDPVDTATYYCARV RGLHRYYYWFAYWGQGTLVT VSSASTKGPSVFPLAPSSKS TSGGTAALGCLVKDYFPEPV TVSWNSGALTSGVHTFPAVL QSSGLYSLSSVVTVPSSSLG TQTYICNVNHKPSNTKVDKK VEPKSCDKTHTCPPCPAPEL LGGPSVFLFPPKPKDTLMIS RTPEVTCVVVDVSHEDPEVK FNWYVDGVEVHNAKTKPREE QYNSTYRVVSVLTVLHQDWL NGKEYKCKVSNKALPAPIEK TISKAKGQPREPQVYTLPPS RDELTKNQVSLTCLVKGFYP SDIAVEWESNGQPENNYKTT PPVLDSDGSFFLYSKLTVDK SRWQQGNVFSCSVMHEALHN HYTQKSLSLSPGK | 59 |
| Light Chain Variable Region Of Modified Antibody (Humanized R28 mAb) | EIVLTQSPATLSLSPGERAT LSCRASSSVSYMHWYQQKPG KSPKPWIYATSNKASGVPSR FSGSGSGTDFTFTISSLQPE DIATYYCQQWSRRPFTFGQG TKVEIKRTVAAPSVFIFPPS DEQLKSGTASVVCLLNNFYP REAKVQWKVDNALQSGNSQE SVTEQDSKDSTYSLSSTLTL SKADYEKHKVYACEVTHQGL SSPVTKSFNRGEC | 60 |

Modified Antibodies

In accordance with this description and the teachings of the art, it is contemplated that in some embodiments, a modified antibody of the invention may comprise one or more alterations, e.g. in one or more CDRs, as compared to the wild type counterpart antibody. The modified antibody would retain substantially the same characteristics required for therapeutic utility as compared to their unmodified wild type counterpart. However, it is thought that certain alterations in amino acid residues at positions described herein would result in a modified antibody with improved or optimized binding affinity for the tumor-associate carbohydrates, compared to the unmodified wild type antibody from which it is generated. In one embodiment, the modified antibody of the present invention is an "affinity matured" antibody.

One type of alterations involves substituting one or more amino acid residues of a CDR of a wild type/unmodified antibody to generate a modified antibody. Such modified antibody may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen-binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such modified antibodies are generated, the panel of variants is subjected to screening using techniques known in the art, including those described herein, and modified antibodies with superior properties in one or more relevant assays may be selected for further development.

The modified antibodies may also be produced by methods described, for example, by Marks et al., 1992, (affinity maturation by variable heavy chain (VH) and variable light chain (VL) domain shuffling), or Barbas, et al., 1994; Shier et al., 1995; Yelton et al., 1995; Jackson et al., 1995; and Hawkins et al., 1992 (random mutagenesis of CDR and/or framework residues).

In one aspect of the invention, the modified antibody or the antigen-binding portion thereof of the present invention comprises a heavy chain variable region wherein the heavy chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively; in which at least one amino acid residue, selected from amino acid residues 28, 31, 57, 63 or 105, is substituted with another amino acid which is different from that present in the unmodified antibody, thereby increasing the binding affinity of the unmodified antibody by about 5%, about 10%, about 20%, about 30%, about 40%, about 50%, about 60%, about 70%, about 80%, about 90%, about 100%, about 150%, about 200%, about 300%, about 400%, about 500%, about 600% or about 700%.

In one embodiment, the heavy chain variable region of the modified antibody comprises at least one of the following amino acid substitutions:
(a) Amino acid residue 28 (Serine) in CDR1 is substituted with a basic amino acid, a neutral amino acid with the proviso that the neutral amino acid is not Serine, or a hydrophobic amino acid,
(b) Amino acid residue 31 (Threonine) in CDR1 is substituted with a basic amino acid,
(c) Amino acid residue 57 (Aspartic Acid) in CDR2 is substituted with a neutral, a basic or a hydrophobic amino acid,
(d) Amino acid residue 63 (Proline) in CDR2 is substituted with a neutral amino acid, a basic amino acid or a hydrophobic amino acid, with the proviso that the hydrophobic amino acid is not Proline, or
(e) Amino acid residue 105 (Aspartic Acid) in CDR3 is substituted with a basic amino acid, a hydrophobic amino acid or a neutral amino acid.

The twenty amino acids are divided into four classes (Basic, Neutral, Hydrophobic and Acidic) according to its side chain. Table 2 lists the four classes of amino acids.

TABLE 2

| Side Chain | Amino Acid |
| --- | --- |
| Basic | Arginine (R), Lysine (K) or Histidine (H) |
| Neutral | Cysteine (C), Tyrosine (Y), Glycine (G), Glutamine (Q), Threonine (T), Asparagine (N) or Serine (S) |
| Hydrophobic | Isoleucine (I), Leucine (L), Methionine (M), Tryptophan (W), Proline (P), Valine (V), Phenylalanine (F) or Alanine (A) |
| Acidic | Aspartic Acid (D) or Glutamic Acid (E) |

Embodiments include modified antibodies with at least one of the following amino acid substitutions in the heavy chain region: (a) Amino acid residue 28 in CDR1 (or the 3rd amino acid residue from the N-terminal of CDR1) is substituted with a basic amino acid, a neutral amino acid other than Serine, Glycine or Glutamine, or a hydrophobic amino acid other than Isoleucine, Leucine, Methionine or Tryptophan, (b) Amino acid residue 31 in CDR1 (or the 6th amino acid residue from the N-terminal of CDR1) is substituted with a basic amino acid other than Histidine, (c) Amino acid residue 57 in CDR2 (or the 6th amino acid residue from the N-terminal of CDR2) is substituted with a neutral amino acid other than Asparagine or Threonine, a basic amino acid or a hydrophobic amino acid other than Isoleucine, Proline or Valine, (d) Amino acid residue 63 in CDR2 (or the 5th amino acid residue from the C-terminal of CDR2) is substituted with a neutral amino acid other than Asparagine, Glutamine or Threonine, a basic amino acid, or a hydrophobic amino acid other than Proline or Methionine, or (e) Amino acid residue I 05 in CDR3 (or the 6th amino acid residue from the N-terminal of CDR3) is substituted with a basic amino acid, a neutral amino acid or a hydrophobic amino acid other than Leucine.

Table 3 provides examples of the amino acid substitution of the heavy chain variable region of the modified antibody. For each substitution, the first letter indicates the amino acid of the unmodified antibody, the number indicates the position according to Kabat numbering scheme, and the second letter indicates the amino acid of the modified antibody. For example, Serine at amino acid residue 28 is substituted with Lysine (S028K) or Arginine (S028R), Tyrosine (S028Y), Phenylalanine (S028F), Threonine at amino acid residue 31 is substituted with Lysine (T031K) or Arginine (T031R), Aspartic Acid at amino acid residue 57 is substituted with Glycine (D057G), Serine (D57S), Glutamine (D057Q), Histidine (D057H) or Tryptophan (D57W), Proline at amino acid residue 63 is substituted with Histidine (P063H), Arginine (P063R), Tyrosine (P063Y), Alanine (P063A), Leucine (P063L) or Valine (P063V), Aspartic Acid at amino acid residue 105 is substituted with Arginine (D105R), Glycine (D105G), Threonine (D105T), Methionine (D105M), Alanine (D105A), Isoleucine (D105I), Lysine (D105K) or Valine (D105V).

TABLE 3

| Substituting Amino acid | Amino Acid Residue 28 | Amino Add Residue 31 | Amino Add Residue 57 | Amino Acid Residue 63 | Amino Acid Residue 105 |
|---|---|---|---|---|---|
| Basic Amino Acid | S028K (SEQ ID NO. 15) S028R (SEQ ID NO. 16) | T031K (SEQ ID NO. 19) T031R (SEQ ID NO. 20) | D057H (SEQ ID NO. 21) | P063H (SEQ ID NO. 26) P063R (SEQ ID NO. 27) | D105R (SEQ ID NO. 32) D105K (SEQ ID NO. 33) |
| Neutral Amino Acid | S028Y (SEQ ID NO. 17) | | D057G (SEQ ID NO. 22) D057S (SEQ ID NO. 23) D057Q (SEQ ID NO. 24) | P063Y (SEQ ID NO. 28) | D105G (SEQ ID NO. 34) D105T (SEQ ID NO. 35) |
| Hydrophobic Amino Acid | S028F (SEQ ID NO. 18) | | D057W (SEQ ID NO. 25) | P063A (SEQ ID NO. 29) P063L, (SEQ ID NO. 30) P063V (SEQ ID NO. 31) | D105M (SEQ ID NO. 36) D105A (SEQ ID NO. 37) D105I (SEQ ID NO. 38) D105V (SEQ ID NO. 39) |

In another aspect of the invention, the modified antibody or the antigen-binding thereof of the present invention comprises a light chain variable region wherein the light chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively; in which at least one amino acid residue, selected from amino acid residues 24, 32, 49, 53 or 93, is substituted with another amino acid which is different from that present in the unmodified antibody, thereby increasing the binding affinity of the unmodified antibody by about 5%, about 10%, about 20%, about 30%, about 40%, about 50%, about 60%, about 70%, about 80%, about 90%, about 100%, about 150%, about 200%, about 300%, about 400%, about 500%, about 600% or about 700%.

In one embodiment, the light chain variable region of the modified antibody comprises at least one of the following amino acid substitutions:
(a) Amino acid residue 24 (Arginine) in CDR1 (or the 1st amino acid residue from the N-terminal of CDR1) is substituted with a neutral amino acid or a hydrophobic amino acid,
(b) Amino acid residue 32 (Methionine) in CDR1 (or the 2nd amino acid residue from the C-terminal of CDR1) is substituted with a neutral amino acid or a hydrophobic amino acid, with the proviso that the hydrophobic amino acid is not Methionine,
(c) Amino acid residue 49 (Alanine) in CDR2 (or the 1st amino acid residue from the N-terminal of CDR2 is substituted with a neutral amino acid,
(d) Amino acid residue 53 (Leucine) in CDR2 (or the 5th amino acid residue from the N-terminal of CDR2) is substituted with a neutral amino acid or a basic amino acid, or
(e) Amino acid residue 93 (Asparagine) in CDR3 (or the 6th amino acid residue from the N-terminal of CDR3) is substituted with a neutral amino acid with the proviso that the neutral amino acid is not Asparagine, a basic amino acid or a hydrophobic amino acid.

Embodiments include modified antibodies with at least one of the following amino acid substitutions in the light chain region: (a) Amino acid residue 24 in CDR1 is substituted with a neutral amino acid other than Threonine or a hydrophobic amino acid other than Methionine, Proline or Valine, (b) Amino acid residue 32 in CDR1 is substituted with a neutral amino acid other than Serine or Threonine, or a hydrophobic amino acid other than Methionine, Leucine or Tryptophan, (c) Amino acid residue 49 in CDR2 is substituted with a neutral amino acid with the proviso that is it not Asparagine or Threonine, (d) Amino acid residue 53 in CDR2 is substituted with a neutral amino acid other than Asparagine or Serine or a basic amino acid other than Arginine, or (e) Amino acid residue 93 in CDR3 is substituted with a neutral amino acid with the proviso that the neutral amino acid is not Asparagine, a basic amino acid or a hydrophobic amino acid with the proviso that the hydrophobic amino acid is not Valine.

Table 4 provides examples of the amino acid substitution of the light chain variable region of the modified antibody. For example, the amino acid residue at 24, using Kabat numbering scheme, is substituted with Glycine (R024G), Serine (R024S) or Tryptophan (R024W), the amino acid residue at 32 is substituted with Glycine (M032G), Glutamine (M032Q) or Valine (M032V), the amino acid residue at 49 is substituted with Glycine (A049G), the amino acid residue at 53 is substituted with Lysine (L053K), Glutamine (L053G), or Threonine (L053T), the amino acid residue at 93 is substituted with Arginine (N093R), Glutamine (N093Q), Serine (N093S), Threonine (N093T), Phenylalanine (N093F), Leucine (N093L), Methionine (N093M).

TABLE 4

| Substituting Amino acid | Amino Acid Residue 24 | Amino Acid Residue 32 | Amino Acid Residue 49 | Amino Acid Residue 53 | Amino Acid Residue 93 |
|---|---|---|---|---|---|
| Basic Amino Acid | | | | L053K (SEQ ID NO. 47) | N093R (SEQ ID NO. 50) |
| Neutral Amino Acid | R024G (SEQ ID NO. 40) | M032G (SEQ ID NO. 43) | A049G (SEQ ID NO. 46) | L053G (SEQ ID NO. 48) | N093Q (SEQ ID NO. 51) |
| | R024S (SEQ ID NO. 41) | M032Q (SEQ ID NO. 44) | | L053T (SEQ ID NO. 49) | N093S (SEQ ID NO. 52) |
| | | | | | N093T (SEQ ID NO. 53) |
| Hydrophobic Amino Acid | R024W (SEQ ID NO. 42) | M032V (SEQ ID NO. 45) | | | N093F (SEQ ID NO. 54) |
| | | | | | N093L (SEQ ID NO. 55) |
| | | | | | N093M (SEQ ID NO. 56) |

In one embodiment, the modified antibody comprises:
(a) a heavy chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively and includes at least one of the following amino acid substitution:
(i) Amino acid residue 28 in CDR1 is substituted with Lysine (S028K), Arginine (S028R), Tyrosine (S028Y) or Phenylalanine (S028F),
(ii) Amino acid residue 31 in CDR1 is substituted with Lysine (T031K) or Arginine (T031R),
(iii) Amino acid residue 57 in CDR2 is substituted with Histidine (D057H), Glycine (D057G), Serine (D057S), Glutamine (D057Q) or Tryptophan (D057W),
(iv) Amino acid residue 63 in CDR2 is substituted with Histidine (P063H), Arginine (P063R), Tyrosine (P063Y), Alanine (P063A), Leucine (P063L) or Valine (P063V),
(v) Amino acid residue 105 in CDR3 is substituted with Arginine (D105R), Glycine (D105G), Threonine (D10ST), Methionine (D105M), Alanine (D105A), Isoleucine (D105I), Lysine (D105K) or Valine (D105V), and/or
(b) a light chain variable region, comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively and includes at least one of the following amino acid substitution:
(i) Amino acid residue 24 in CDR1 is substituted with Glycine (R024G), Serine (R024S) or Tryptophan (R024W),
(ii) Amino acid residue 32 in CDR1 is substituted with Glycine (M032G), Glutamine (M032Q) or Valine (M032V),
(iii) Amino acid residue 49 in CDR2 is substituted with Glycine (A049G),
(iv) Amino acid residue 53 in CDR2 is substituted with Lysine (L053K), Glutamine (L053G), or Threonine (L053T), Amino acid residue 93 in CDR3 is substituted with Arginine (N093R), Glutamine (N093Q), Serine (N093S), Threonine (N093T), Phenylalanine (N093F), Leucine (N093L) or Methionine (N093M).

In another embodiment, the modified antibody comprises:
(c) a heavy chain variable region comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 1, 2 and 3 respectively and includes at least one of the following amino acid substitution:
(i) Amino acid residue 28 in CDR1 is substituted with Arginine (S028R),
(ii) Amino acid residue 31 in CDR1 is substituted with Arginine (T031R),
(iii) Amino acid residue 57 in CDR2 is substituted with Glycine (D057G),
(iv) Amino acid residue 63 in CDR2 is substituted with Tyrosine (P063Y),
(v) Amino acid residue 105 in CDR3 is substituted with Arginine (D105R), and/or
(d) a light chain variable region, comprises three CDRs, CDR1, CDR2 and CDR3, having amino acid sequences about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence set forth in SEQ ID NOs: 7, 8 and 9 respectively and includes at least one of the following amino acid substitution:
(i) Amino acid residue 24 in CDR1 is substituted with Tryptophan (R024W),
(ii) Amino acid residue 32 in CDR1 is substituted with Glutamine (M032Q), (iii) Amino acid residue 49 in CDR2 is substituted with Glycine (A049G),
(iv) Amino acid residue 53 in CDR2 is substituted with Lysine (L053K),
(v) Amino acid residue 93 in CDR3 is substituted with Arginine (N093R).

In yet another embodiment, the present invention provides a modified antibody or the antigen-binding portion thereof, comprising
(e) a heavy chain and a light chain, wherein the heavy chain having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence selected from SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, and/or
(b) a light chain, wherein the light chain having an amino acid sequence about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the amino acid sequence selected from SEQ ID NO.40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55 or SEQ ID NO. 56.

In other embodiments, the variable regions of the modified antibodies or the antigen-binding portions thereof described herein do not include the amino acid substitutions listed in FIG. 5.

Any of a variety of tumor associated carbohydrate antigens, particularly Globo H, may be used in the practice of the present invention. Examples of tumor-associate carbohydrate antigens include, but are not limited to Globo antigens such as Globo H, stage-specific embryonic antigen 3 (SSEA-3) (also called Gb5), stage-specific embryonic antigen 4 (SSEA-4), Gb4 and Gb3, Lewis antigens such as sLe$^x$, Le$^x$ sLe$^a$, Le$^a$ and Le$^y$, mucin glycans such as sTn, Tn and Thomsen-Friedenreich antigen (TF), the ganglioside such as GD1a, GT1b, A2B5, GD2, GD3, Fucosyl GMI, GMI, GM2, GM3, Neu5GcGM3 and polysialic acid (PSA), sulfitide antigen such as 6Gal-HSO$_3$-SiaLex and 6GluNAc-HSO$_3$-SiaLex. Other carbohydrate antigens include, but are not limited to: α-Galactose, α-Man-6-phosphate, α-L-Rhamnose, α-GalNAc(Tn), α-NeuAc-OCH$_2$C$_6$H$_4$-p-NHCOOCH$_2$, Fucα1-2Galβ1-4GalNAcβ (H types 3), NeuAcα2-8NeuAcα, (NeuAcα2-8)2 Polysialic acid, NeuAca2-6Galb, NeuAcb2-6Gala(STn), Gala1-3Galb1-4GlaNAcb (NeuAca2-8)3, GalNAcαa-3(Fucα1-2)Galβ (Blood Group A), Galα1-3(Fucα1-2)Galβ (Blood Group B), 6Gal-HSO$_3$-SiaLex, 6GluNAc-HSO$_3$-SiaLex and α2-6 sialylated diantennary N-glycans.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose diseases, such as cancer.

The antibodies or antigen-binding portions thereof can be used on cells in culture, e.g., in vitro or ex vivo. For example, cells can be cultured in vitro in culture medium and contacted by the antibody or the antigen-binding portion thereof. The methods can be performed on cells present in a subject, as part of an in vivo (e.g., therapeutic or prophylactic) protocol. For in vivo embodiments, the contacting step is effected in a subject and includes administering the antibody or the antigen-binding portion thereof to the subject under conditions effective to permit binding of the antibody, or the antigen-binding portion thereof, to a tumor-associate carbohydrate antigen (e.g., Globo H) expressed on one or more cancer cells in the subject, e.g., in the breast cancer cell.

METHODS FOR INHIBITING CANCER CELLS

Antibodies or the antigen-binding portions thereof of the present invention are capable of modulating, decreasing, antagonizing, mitigating, alleviating, blocking, inhibiting, abrogating and/or interfering with at least one tumor-associate carbohydrate antigen or a fragment thereof in vitro, in situ and/or in vivo.

The invention also provides methods for inhibiting the growth of a cell in vitro, ex vivo or in vivo, wherein the cell, such as a cancer cell, is contacted with an effective amount of an antibody or an antigen-binding portion thereof as described herein. Pathological cells or tissue such as hyper-proliferative cells or tissue may be treated by contacting the cells or tissue with an effective amount of an antibody or an antigen-binding portion thereof of this invention. The cells, such as cancer cells, can be primary cancer cells or can be cultured cells available from tissue banks such as the American Type Culture Collection (ATCC). The pathological cells can be cells of a Globo H expressing cancer, gliomas, meningioma, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) Intern. J. Mol. Med. 10:785-788. Thorne, et al. (2004) Neuroscience 127:481-496. Fernandes, etal. (2005) Oncology Reports 13:943-947. Dafonseca, etal. (2008) Surgical Neurology 70:259267. Da Fonseca, et al. (2008) Arch. Immunol. Ther. Exp. 56:267-276. Hashizume, et al. (2008) Neuroncology 10:112-120. In one embodiment, the cancer is Globo H expressing cancer. In another embodiment, the cancer is SSEA-3 expressing cancer. In yet another embodiment, the cancer is SSEA-4 expressing cancer. Globo H expressing cancer, SSEA-3 expressing cancer and SSEA-4 expressing cancer include one or more of sarcoma, skin cancer, leukemia, lymphoma, brain cancer, glioblastoma, lung cancer, breast cancer, oral cancer, head-and-neck cancer, nasopharyngeal cancer, esophageal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testicular cancer, buccal cancer, oropharyngeal cancer, laryngeal cancer and/or prostate cancer. In one aspect, the method comprises the assaying of a sample selected from one or more of breast, ovary, lung, pancreatic, stomach (gastric), colorectal, prostate, liver, cervix, esophagus, brain, oral, and/or kidney cancer.

In vitro efficacy of the present antibody or the antigen-binding portion thereof can be determined using methods well known in the art. MTT assay is based on the principle of uptake of MTT, a tetrazolium salt, by metabolically active cells where it is metabolized into a blue colored formazan product, which can be read spectrometrically. J. ofImmunological Methods 65: 55 63, 1983. The cytotoxicity of the present antibody or the antigen-binding portion thereof may be studied by colony formation assay. Functional assays for binding Globo H antigen may be performed via ELISA Cell cycle block by the antibody or the antigen-binding thereof may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays. Assays can also be done in vivo using a murine model. See, e.g., B. Teicher, Tumor Models for Efficacy Determination. Mol Cancer Ther 2006; 5: 2435-2443."

Pharmaceutical Composition

In some embodiments, the present invention provides pharmaceutical compositions comprising an antibody or antigen-binding portion thereof described herein, and a pharmaceutically acceptable carrier. Pharmaceutically acceptable carriers include any and all solvents, dispersion media, isotonic and absorption delaying agents, and the like that are physiologically compatible. In one embodiment, the pharmaceutical composition is effective to inhibit cancer cells in a subject.

Routes of administration of the present pharmaceutical compositions include, but are not limited to, intravenous, intramuscular, intranasal, subcutaneous, oral, topical, subcutaneous, intradermal, transdermal, subdermal, parenteral, rectal, spinal, or epidermal administration.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or the active ingredient encapsulated in liposome vehicles or other particulate carriers used for sustained delivery. For example, the pharmaceutical composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

Naturally, the pharmaceutical compositions to be used for in vivo administration must be sterile; sterilization may be accomplished be conventional techniques, e.g. by filtration through sterile filtration membranes. It may be useful to increase the concentration of the antibody to come to a so-called high concentration liquid formulation (HCLF); various ways to generate such HCLFs have been described.

The pharmaceutical composition are administered alone, and/or mixed with another therapeutic agent, for example, a second monoclonal or polyclonal antibody or the antigen-binding portion thereof or an anti-cancer agent such as DNA damaging or tubulin binding agents, or agents which inhibit angiogenesis, signal transduction pathways or mitotic checkpoints. The combination product may be a mixture of the two ingredients or they may be covalently attached. In one example, the antibody or antigen-binding portion thereof specifically binds to Globo His combined with an antibody (monoclonal or polyclonal) or antigen-binding portion thereof specifically binds VEGF. In another example, the second agent is a chemotherapy agent (e.g., cyclophosphamide, 5-fluorouracil or Actinomycin-D). The antibodies can also be administered in combinations with a cancer vaccine, e.g., Globo H conjugated with Diphtheria Toxin and a saponin adjuvant. The additional therapeutic agent may be administered simultaneously with, optionally as a component of the same pharmaceutical preparation, or before or after administration of the claimed antibody of the invention. Actual methods of preparing such dosage forms are known, or will be modified, to those skilled in the art. See, e.g., Remington's Pharmaceutical Sciences, Mack Publishing Company, Easton, Pa., 21 st edition.

Pharmaceutical compositions can be administered in a single dose treatment or in multiple dose treatments on a schedule and over a time period appropriate to the age, weight and condition of the subject, the particular composition used, and the route of administration, whether the pharmaceutical composition is used for prophylactic or curative purposes, etc. For example, in one embodiment, the pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an antibody according to the invention, e.g., the period of time over which the pharmaceutical composition is administered, can vary, depending on any of a variety of factors, e.g., subject response, etc. For example, the pharmaceutical composition can be administered over a period of time ranging from about one or more seconds to one or more hours, one day to about one week, from about two weeks to about four weeks, from about one month to about two months, from about two months to about four months, from about four months to about six months, from about six months to about eight months, from about eight months to about l year, from about I year to about 2 years, or from about 2 years to about 4 years, or more.

For ease of administration and uniformity of dosage, oral or parenteral pharmaceutical compositions in dosage unit form may be used. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. In one embodiment, the dosage of such compounds lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture.

Sonderstrup, Springer, Sem. Immunopathol. 25: 35-45, 2003. Nikula et al., Inhal. Toxicol. 4(12): 123-53, 2000.

An exemplary, non-limiting range for a therapeutically or prophylactically effective amount of an antibody or antigen-binding portion of the invention is from about 0.001 to about 60 mg/kg body weight, about 0.01 to about 30 mg/kg body weight, about 0.01 to about 25 mg/kg body weight, about 0.5 to about 25 mg/kg body weight, about 0.1 to about 20 mg/kg body weight, about 10 to about 20 mg/kg body weight, about 0.75 to about 10 mg/kg body weight, about 1 to about 10 mg/kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight.

The pharmaceutical composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging from about 0.01 mg to about 10 g, from about 0.1 mg to about 9 g, from about 1 mg to about 8 g, from about 2 mg to about 7 g, from about 3 mg to about 6 g, from about 10 mg to about 5 g, from about 20 mg to about 1 g, from about 50 mg to about 800 mg, from about 100 mg to about 500 mg, from about 0.01 μg to about 10 g, from about 0.05 μg to about 1.5 mg, from about 10 μg to about 1 mg protein, from about 30 μg to about 500 μg, from about 40 μg to about 300 μg, from about 0.1 μg to about 200 μg, from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy and can be determined by one of ordinary skill in the art without undue experimentation.

The present antibodies, antigen-binding portions thereof, pharmaceutical compositions and methods of use are applicable and can be used in all vertebrates, e.g., mammals and non-mammals, including human, mice, rats, guinea pigs, hamsters, dogs, cats, cows, horses, goats, sheep, pigs, monkeys, apes, gorillas, chimpanzees, rabbits, ducks, geese, chickens, amphibians, reptiles and other animals.

The following examples of specific aspects for carrying out the present invention are offered for illustrative purposes only, and are not intended to limit the scope of the present invention in any way.

EXAMPLES

Example 1

Generation of Modified Antibody

The wild type humanized antibody, with a heavy chain variable region comprising SEQ ID NO. 13 and a light chain variable region comprising SEQ ID NO. 14, and wild type chemirice antibody, with a heavy chain variable region comprising SEQ ID NO. 57 and a light chain variable region comprising SEQ ID NO. 58, were derived from the non-human antibody of hybridoma 2C2. FIG. 1 illustrates the amino acid sequence of the heavy chain variable region (FIG. 1A; one hundred and twelve amino acid residues) and the light chain variable region (FIG. 1B: ninety-six amino acid residues) of the unmodified humanized antibody. Please referred to the PCT patent application (application number: PCT/US15/25305) for more details regarding the experimental procedure.

The modified antibodies of the present invention was generated using the following two-steps: (1) Comprehensive Positional Evolution, followed by (2) Combinatorial Protein Synthesis.

Example 2

Binding Affinity Comparison of Chimeric and Humanized Antibodies

An in vitro evaluation of the binding affinity of the unmodified chimeric and humanized antibodies from Example 1 was performed, using ELISA. FIG. 2 illustrated the $OD_{450}$ nm of the chimeric antibody (Heavy chain: SEQ ID NO. 57 and Light chain: SEQ ID NO. 58) and the humanized antibody (Heavy chain: SEQ ID NO. 13 and Light chain: SEQ ID NO. 14). The OD value of the chimeric antibody (Heavy chain: SEQ ID NO. 57 and Light chain: SEQ ID NO. 58) was 0.89 and the OD value of the humanized antibody (Heavy chain: SEQ ID NO. 13 and Light chain: SEQ ID NO. 14) was only 0.34. The lower OD value of the humanized antibody indicated that the following CDR sequence modification/mutation of the unmodified humanized antibody is necessary.

Example 3

Comprehensive Positional Evolution

Referring to FIG. 3, at least 10 amino acid mutant/substitutions were created for each amino acid residue within the three heavy chain and light chain CDRs of the unmodified humanized antibody (SEQ ID NOs: 1-3 and 7-8) using the Comprehensive Positional Evolution technology (BioAtala, USA). Twenty-six amino acid residues in the light chain CDRs and forty-one amino acid residues in the heavy chain CDRs were identified, with a total of 670 Comprehensive Positional Evolution mutants created, 260 of which were in the light chain CDRs and 410 of which were in the heavy chain CDRs.

FIGS. 4A-4E illustrated the $OD_{450}$ nm of the modified antibody with a single Comprehensive Positional Evolution amino acid mutant substitution at residue 28 (FIG. 4A), residue 31 (FIG. 4B), residue 57 (FIG. 4C), residue 63 (FIG. 4D) and residue 105 (FIG. 4E) of the heavy chain variable region and that of the wild type chimeric antibody. FIGS. 5A-5E illustrated $OD_{450}$ nm of modified antibodies with a single Comprehensive Positional Evolution amino acid mutant substitution at residue 24 (FIG. 5A), residue 32 (FIG. 5B), residue 49 (FIG. 5C), residue 53 (FIG. 5D) and residue 93 (FIG. 5E) of the light chain variable region and that of the wild type chimeric antibody.

The following ten Comprehensive Positional Evolution mutants were chosen to undergo Combinatorial Protein Synthesis, based on their binding activities to Globo-H ceramide and expression screening: Heavy Chain (HC)—

S028R, HC-T031R, HC-D057G, HC—P063Y, HC-D105R, Light Chain (LC)-R024W, LC-M032Q, LC-A049G, LC-L053K and LC-N093R.

Example 4

Combinatorial Protein Synthesis

A Combinatorial Protein Synthesis library of the 10 chosen Comprehensive Positional Evolution mutants in Example 3 was created, containing all possible combinations of these 10 chosen Comprehensive Positional Evolution mutants (a total of 930 Combinatorial Protein Synthesis mutants).

The 930 Combinatorial Protein Synthesis mutants were transfected into CHO—S cells in 96 well format, cultured at 37° C. in DMEM with 10% serum and expressed as full length IgG1 molecules. Supernatant was collected at 48 hours post transfection. Concentration of IgG in the supernatant was determined using the ELISA protocol for quantification of human IgGs. IgG in the cell culture supernatant was captured on the plate with anti-human-IgG Fc antibody. Bound IgG was detected with anti-human-IgG conjugated with HRP (Promega, USA). Concentration of the IgG was calculated using commercial available human IgG as standard. Supernatants were adjusted to 50 ng/ml and tested for binding to Globo-H ceramide using affinity ELISA protocol. The unmodified chimeric antibody were used as controls in the ELISA plates. The reactions were stopped with 1N HCl after TMB was added to the wells and were read immediately. $OD_{450}$ nm value of the reaction was measured with SpectraMax Plus (Molecular Devices, USA).

FIG. 6 illustrated six hundred and sixty-nine Combinatorial Protein Synthesis mutants with a higher $OD_{450}$ nm value comparing to that of the unmodified chimeric antibody (Heavy chain: SEQ ID NO. 57 and Light chain: SEQ ID NO. 58). The higher OD value indicates a stronger binding affinity to Globo H.

FIG. 7 illustrated the dissociation constant (Kd) of chimeric antibody obtained from hybridoma VK9 (originated from Memorial Sloan Kettering Cancer Center, MSKCC), chimeric antibody derived from hybridoma 2C2 (the amino acid of the heavy chain is SEQ ID NO: 57 and the amino acid sequence of the light chain is SEQ ID NO:58), and an exemplary embodiment of the modified antibody (human R28 mAbs, wherein the amino acid of the heavy chain is SEQ ID NO: 59 and the amino acid sequence of the light chain is SEQ ID NO: 60). It shows the chimeric antibody derived from hybridoma 2C2 (8.60E-07) and humanized R28 mAb (5.04E-07) have better binding affinities compare to VK9 (1.21E-05) antibody.

Example 5

In Vivo Anti-Tumor Evaluation of Anti-Globo H Antibodies

Figure 8:
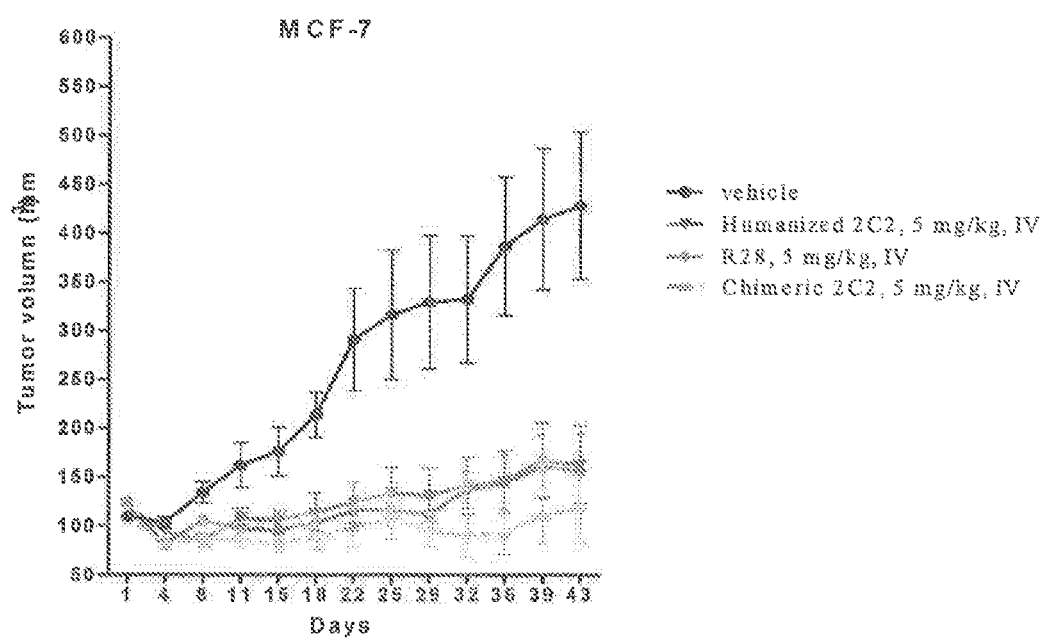
FIG. 8 illustrates a linear plot showing the effect of normal saline (Vehicle), chimeric antibody derived from hybridoma 2C2 (SEQ ID NOs: 57 and 58), humanized antibody derived from hybridoma 2C2 (SEQ ID NOs: 13 and 14) and one exemplary embodiment of the modified antibody (humanized R28 mAbs, SEQ ID NOs: 59 and 60) on breast cancer (MCF7) volume in mice.

Nude mice weighing 27 g with human breast cancer (MCF7) xenograft were injected with 5 mg/kg of chimeric antibody derived from hybridoma 2C2 (SEQ ID NOs: 57 and 58), humanized antibody of hybridoma 2C2 (SEQ ID NOs: 13 and 14) or humanized R28 antibodies (SEQ ID NOs: 59 and 60). The mice were observed for a period of 18 days for tumor volume and the results were recorded and summarized in FIG. 8. The tumor volume was calculated by the formula: $(Length \times Width)^2/2$. As shown in FIG. 8, the tumor volumes of the modified antibodies (chimeric 2C2, humanized 2C2 and humanized R28) were significantly reduced compared to that of the control group (vehicle only) ($P<0.05$) since Day 8.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference in its entirety for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method for inhibiting proliferation of a cancer cell, comprising:
   contacting the cancer cell with an effective amount of an antibody, or antigen-binding portion thereof, that binds to a carbohydrate antigen, wherein the antibody, or antigen-binding portion thereof, comprises a heavy chain variable region and a light chain variable region comprising:
   a heavy chain complementarity determining region HC-CDR1 selected from the group consisting of:
   (i) SEQ ID NO: 1,
   (ii) SEQ ID NO: 1 wherein amino acid residue 3 is substituted with an arginine (S028R), and
   (iii) SEQ ID NO: 1 wherein amino acid residue 6 is substituted with an arginine (T031R),
   a heavy chain complementarity determining region HC-CDR2 selected from the group consisting of:
   (i) SEQ ID NO: 2,
   (ii) SEQ ID NO: 2 wherein amino acid residue 6 is substituted with a glycine (D057G), and
   (iii) SEQ ID NO: 2 wherein amino acid residue 12 is substituted with a tyrosine (P063Y),
   a heavy chain complementarity determining region HC-CDR3 selected from the group consisting of:
   (i) SEQ ID NO: 3, and
   (ii) SEQ ID NO: 3 wherein amino acid residue 6 is substituted with an arginine (D105R),
   a light chain complementarity determining region LC-CDR1 selected from the group consisting of:
   (i) SEQ ID NO: 7,
   (ii) SEQ ID NO: 7 wherein amino acid residue 1 is substituted with a tryptophan (R024W), and
   (iii) SEQ ID NO: 7 wherein amino acid residue 9 is substituted with a glutamine (M032Q),
   a light chain complementarity determining region LC-CDR2 selected from the group consisting of:
   (i) SEQ ID NO: 8,
   (ii) SEQ ID NO: 8 wherein amino acid residue 1 is substituted with a glycine (A049G), and
   (iii) SEQ ID NO: 8 wherein amino acid residue 5 is substituted with a lysine (L053K), and
   a light chain complementarity determining region LC-CDR3 selected from the group consisting of:
   (i) SEQ ID NO: 9, and
   (ii) SEQ ID NO: 9 wherein amino acid residue 6 is substituted with an arginine (N093R),
   wherein the antibody, or an antigen-binding portion thereof comprises at least one of the amino acid substitutions in a CDR region selected from the group consisting of S028R, T031R, D057G, P063Y, D105R, R024W, M032Q, A049G, L053K and N093R.

2. The method of claim 1, wherein the antibody or antigen-binding portion thereof further comprises at least one of the following frameworks:
   (a) a heavy chain framework (HC-FW1) having a sequence 90% to 100% homologous to SEQ ID NO: 4,
   (b) a heavy chain framework (HC-FW2) having a sequence 90% to 100% homologous to SEQ ID NO: 5,
   (c) a heavy chain framework (HC-FW3) having a sequence 90% to 100% homologous to SEQ ID NO: 6,
   (d) a heavy chain framework (HC-FW2) having a sequence 90% to 100% homologous to SEQ ID NO: 5, wherein amino acid residue 9 in HC-FW2 is glycine and not substituted,
   (e) a light chain framework (LC-FW1) having a sequence 90% to 100% homologous to SEQ ID NO: 10,
   (f) a light chain framework (LC-FW2) having a sequence 90% to 100% homologous to SEQ ID NO: 11,
   (g) a light chain framework (LC-FW3) having a sequence 90% to 100% homologous to SEQ ID NO: 12,
   (h) a light chain framework (LC-FW2) having a sequence 90% to 100% homologous to SEQ ID NO: 11, wherein amino acid residue 12 in LC-FW2 is proline and not substituted, and/or (i) a light chain framework (LC-FW2) having a sequence 90% to 100% homologous to SEQ ID NO: 11, wherein amino acid residue 13 in LC-FW2 is tryptophan and not substituted.

3. The method of claim 1, wherein the carbohydrate antigen is Globo H, stage-specific embryonic antigen 3 (SSEA-3), stage-specific embryonic antigen 4 (SSEA-4), Gb4, Gb3, sLe$^x$, Le$^x$, sLe$^a$, Le$^a$, Le$^y$, polysialic acid (PSA), sTn, Tn, TF, GD1, GD2, GD3, Fucosyl GM1, GM1, GM2, GM3, GD1a, GM2, 6Gal-HSO$_3$-SiaLe$^x$ or 6GluNAc-HSO$_3$-SiaLe$^x$.

4. The method of claim 1, wherein the cancer is a Globo H, SSEA-3 or SSEA-4 expressing cancer.

5. The method of claim 1, wherein the cancer is selected from the group consisting of sarcomas, skin cancer, leukemia, lymphoma, brain cancer, glioblastoma, lung cancer, breast cancer, oral cancer, head-and-neck cancer, nasopharyngeal cancer, esophageal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testicular cancer, buccal cancer, oropharyngeal cancer, laryngeal cancer, hematopoietic cancer and prostate cancer.

6. A method for treating cancer, comprising:
   administering to a subject in need of such treatment an effective amount of a pharmaceutical composition comprising:
   an antibody, or antigen-binding portion thereof, that binds to a carbohydrate antigen; and
   a pharmaceutical acceptable carrier,
   wherein the antibody, or antigen-binding portion thereof, comprises a heavy chain variable region and a light chain variable region comprising:
   a heavy chain complementarity determining region HC-CDR1 selected from the group consisting of:
   (i) SEQ ID NO: 1,
   (ii) SEQ ID NO: 1 wherein amino acid residue 3 is substituted with an arginine (S028R), and
   (iii) SEQ ID NO: 1 wherein amino acid residue 6 is substituted with an arginine (T031R),
   a heavy chain complementarity determining region HC-CDR2 selected from the group consisting of:
   (i) SEQ ID NO: 2,
   (ii) SEQ ID NO: 2 wherein amino acid residue 6 is substituted with a glycine (D057G), and
   (iii) SEQ ID NO: 2 wherein amino acid residue 12 is substituted with a tyrosine (P063Y1),
   a heavy chain complementarity determining region HC-CDR3 selected from the group consisting of:
   (i) SEQ ID NO: 3, and
   (ii) SEQ ID NO: 3 wherein amino acid residue 6 is substituted with an arginine (D105R),
   a light chain complementarity determining region LC-CDR1 selected from the group consisting of:
   (i) SEQ ID NO: 7,
   (ii) SEQ ID NO: 7 wherein amino acid residue 1 is substituted with a tryptophan (R024W), and
   (iii) SEQ ID NO: 7 wherein amino acid residue 9 is substituted with a glutamine (M032Q), a light chain complementarity determining region LC-CDR2 selected from the group consisting of:
(i) SEQ ID NO: 8,
(ii) SEQ ID NO: 8 wherein amino acid residue 1 is substituted with a glycine (A049G), and
(iii) SEQ ID NO: 8 wherein amino acid residue 5 is substituted with a lysine (L053K), and a light chain complementarity determining region LC-CDR3 selected from the group consisting of:
(i) SEQ ID NO: 9, and
(ii) SEQ ID NO: 9 wherein amino acid residue 6 is substituted with an arginine (N093R), wherein the antibody, or an antigen-binding portion thereof, comprises at least one of the amino acid substitutions in a CDR region selected from the group consisting of S028R, T031R, D057G, P063Y, D105R, R024W, M032Q, A049G, L053K and N093R.

7. The method of claim 6, wherein the antibody, or antigen-binding portion thereof, further comprises at least one of the following frameworks:
(a) a heavy chain framework (HC-FW1) having a sequence 90% to 100% homologous to SEQ ID NO: 4,
(b) a heavy chain framework (HC-FW2) having a sequence 90% to 100% homologous to SEQ ID NO: 5,
(c) a heavy chain framework (HC-FW3) having a sequence 90% to 100% homologous to SEQ ID NO: 6,
(d) a heavy chain framework (HC-FW2) having a sequence 90% to 100% homologous to SEQ ID NO: 5, wherein amino acid residue 9 in HC-FW2 is glycine and not substituted,
(e) a light chain framework (LC-FW1) having a sequence 90% to 100% homologous to SEQ ID NO: 10,
(f) a light chain framework (LC-FW2) having a sequence 90% to 100% homologous to SEQ ID NO: 11,
(g) a light chain framework (LC-FW3) having a sequence 90% to 100% homologous to SEQ ID NO: 12,
(h) a light chain framework (LC-FW2) having a sequence 90% to 100% homologous to SEQ ID NO: 11, wherein amino acid residue 12 in LC-FW2 is proline and not substituted, and/or
(i) a light chain framework (LC-FW2) having a sequence 90% to 100% homologous to SEQ ID NO: 11, wherein amino acid residue 13 in LC-FW2 is tryptophan and not substituted.

8. The method of claim 6, wherein the carbohydrate antigen is Globo H, stage-specific embryonic antigen 3 (SSEA-3), stage-specific embryonic antigen 4 (SSEA-4), Gb4, Gb3, sLe$^x$, Le$^x$, sLe$^a$, Le$^a$, Le$^y$, polysialic acid (PSA), sTn, Tn, TF, GD1, GD2, GD3, Fucosyl GM1, GM1, GM2, GM3, GD1a, GM2, 6Gal-HSO$_3$-SiaLe$^x$ or 6GluNAc-HSO$_3$-SiaLe$^x$.

9. The method of claim 6, wherein the cancer is a Globo H, SSEA-3 or SSEA-4 expressing cancer.

10. The method of claim 6, wherein the subject is human.

11. The method of claim 6, wherein the cancer is a glioma, meningioma or pituitary adenoma.

12. The method of claim 6, wherein the cancer is a CNS metastasis from a systemic cancer.

13. The method of claim 6, wherein the cancer is selected from the group consisting of sarcomas, skin cancer, leukemia, lymphoma, brain cancer, glioblastoma, lung cancer, breast cancer, oral cancer, head-and-neck cancer, nasopharyngeal cancer, esophageal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testicular cancer, buccal cancer, oropharyngeal cancer, laryngeal cancer, hematopoietic cancer and prostate cancer.

14. The method of claim 6, wherein the pharmaceutical composition is administered by intravenous, intramuscular, intranasal, subcutaneous, oral, topical, subcutaneous, intradermal, transdermal, subdermal, parenteral, rectal, spinal, or epidermal administration.

15. The method of claim 6, wherein the pharmaceutical composition further comprises at least one therapeutic agent.

16. The method of claim 15, wherein the therapeutic agent is a monoclonal antibody, polyclonal antibody or an anti-cancer agent.

17. The method of claim 16, wherein the anti-cancer agent is DNA damaging or tubulin binding agents, or agents which inhibit angiogenesis, signal transduction pathways or mitotic checkpoints.

* * * * *